(12) United States Patent
Goto et al.

(10) Patent No.: US 9,585,828 B2
(45) Date of Patent: Mar. 7, 2017

(54) PROTEOGLYCAN-CONTAINING MATERIAL

(71) Applicants: SUNSTAR INC., Osaka (JP); HIROSAKI UNIVERSITY, Aomori (JP)

(72) Inventors: Masashi Goto, Osaka (JP); Kazushi Yamamoto, Osaka (JP); Youji Katou, Aomori (JP); Yohtaro Katagata, Aomori (JP); Seiko Itou, Aomori (JP)

(73) Assignees: SUNSTAR INC., Osaka (JP); HIROSAKI UNIVERSITY, Aomori (JP)

(*) Notice: Subject to any disclaimer, the term of this patent is extended or adjusted under 35 U.S.C. 154(b) by 55 days.

(21) Appl. No.: 14/046,160

(22) Filed: Oct. 4, 2013

(65) Prior Publication Data
US 2014/0080761 A1    Mar. 20, 2014

Related U.S. Application Data

(63) Continuation of application No. 13/383,987, filed as application No. PCT/JP2010/062125 on Jul. 16, 2010, now abandoned.

(30) Foreign Application Priority Data

Jul. 16, 2009 (JP) ................................ 2009-168123

(51) Int. Cl.
| | |
|---|---|
| *A61K 38/14* | (2006.01) |
| *A61K 8/64* | (2006.01) |
| *A23F 3/30* | (2006.01) |
| *A61K 35/60* | (2006.01) |
| *A61Q 11/00* | (2006.01) |
| *A61Q 19/00* | (2006.01) |
| *A61Q 19/08* | (2006.01) |
| *C08B 37/00* | (2006.01) |
| *A61K 8/73* | (2006.01) |
| *A23G 3/36* | (2006.01) |
| *A23G 4/06* | (2006.01) |

(52) U.S. Cl.
CPC .................. *A61K 8/64* (2013.01); *A23F 3/30* (2013.01); *A23L 29/275* (2016.08); *A23L 33/17* (2016.08); *A61K 8/735* (2013.01); *A61K 35/60* (2013.01); *A61Q 11/00* (2013.01); *A61Q 19/00* (2013.01); *A61Q 19/08* (2013.01); *C08B 37/0066* (2013.01); *A23G 3/36* (2013.01); *A23G 4/06* (2013.01); *A23V 2002/00* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 3,862,003 A | 1/1975 | Okuyama et al. | |
| 4,350,682 A | 9/1982 | Balassa | |
| 4,473,551 A | 9/1984 | Schinitsky | |
| 6,347,986 B1 | 2/2002 | Fujii | |
| 7,504,115 B2 | 3/2009 | Kralovec et al. | |
| 2002/0045735 A1 | 4/2002 | Takagaki | |
| 2004/0234617 A1 | 11/2004 | Pang et al. | |
| 2005/0070500 A1* | 3/2005 | Boucher et al. ................ 514/54 |
| 2005/0130272 A1 | 6/2005 | Kachi | |
| 2006/0258570 A1* | 11/2006 | Hook et al. ........................ 514/8 |
| 2007/0010430 A1* | 1/2007 | Sato ........................ A61K 35/60 |
| | | | 514/20.2 |
| 2009/0253794 A1* | 10/2009 | Tomono et al. ............... 514/563 |
| 2010/0234580 A1 | 9/2010 | Kudo et al. | |
| 2012/0157391 A1 | 6/2012 | Goto et al. | |

FOREIGN PATENT DOCUMENTS

| | | | |
|---|---|---|---|
| CN | 1436537 | * | 8/2003 |
| CN | 1654670 | | 8/2005 |
| CN | 1761686 | | 4/2006 |
| CN | 101230369 | | 7/2008 |
| CN | 101358220 | | 2/2009 |

(Continued)

OTHER PUBLICATIONS

Kalman et al, Effect of a natural extract of chicken combs with a high content of hyaluronic acid (Hyal-Joint®) on pain relief and quality of life in subjects with knee osteoarthritis: a pilot randomized double-blind placebo-controlled trial, Nutrition Journal 2008, 7:3.*
"Causes of Aging Skin" from AgingSkinNet [online], [Retrieved on May 12, 2014]. Retrieved from URL: <http://www.skincarephysicians.com/agingskinnet/basicfacts.html >.*
International Search Report issued Sep. 7, 2010 in International (PCT) Application No. PCT/JP2010/062125.
K. Fujii, "Sake•Masu Tobu Riyo ni yoru Kinosei Shokuhin no Kaihatsu", Technical Report of Japan Food Industry Center, No. 28, pp. 11-14, 2002.
K. Hatae et al., "Effects of Vineger-Curing on the Chemical and Physical Properties of the Salmon-Nose-Cartilage", Nippon Shokuhin Kogyo Gakkaishi, vol. 37, No. 7, pp. 505-510, 1990 (with English abstract).
Supplementary European Search Report dated Jan. 30, 2013 in corresponding European Patent Application No. 10799943.5.
International Search Report and Written Opinion, with partial English translation, mailed Apr. 3, 2012 in International Application No. PCT/JP2012/051131.
Masutani et al., "Anti-aging effect of proteoglycan from salmon nasal cartilage", Food Style 21, Aug. 1, 2010, vol. 14, No. 8, pp. 49-52.

(Continued)

*Primary Examiner* — James H Alstrum Acevedo
*Assistant Examiner* — Sergio Coffa
(74) *Attorney, Agent, or Firm* — Wenderoth, Lind & Ponack, L.L.P.

(57) ABSTRACT

The present invention was made in view of an object to produce a novel proteoglycan-containing material, and find a novel use and/or a superior effect of the proteoglycan-containing material. The present invention provides a proteoglycan-containing material obtained from fish cartilage, wherein the proteoglycan-containing material comprises an acidic saccharide component having a molecular weight of not less than 2000 kDa. The proteoglycan-containing material provides advantageous effects for skin-moisturizing and skin anti-aging, including a superior skin fibroblast proliferation effect, an effect of enhancing and improving the skin barrier function, an effect of enhancing and improving the skin's capability to produce collagen, a dermis-thickening inhibition effect, and the like.

6 Claims, 14 Drawing Sheets

(56) References Cited

FOREIGN PATENT DOCUMENTS

| | | |
|---|---|---|
| EP | 1 570 845 | 9/2005 |
| EP | 1 614 697 | 1/2006 |
| JP | 49-26234 | 3/1974 |
| JP | 2000-175617 | 6/2000 |
| JP | 2001-172296 * | 6/2001 |
| JP | 2001-509513 | 7/2001 |
| JP | 2002-069097 | 3/2002 |
| JP | 2003-055255 | 2/2003 |
| JP | 2003-299497 | 10/2003 |
| JP | 2003-300858 A | 10/2003 |
| JP | 2005-75740 | 3/2005 |
| JP | 2005-113106 | 4/2005 |
| JP | 2006-143605 | 6/2006 |
| JP | 2007-063177 | 3/2007 |
| JP | 2007-252212 | 10/2007 |
| JP | 2007-262103 | 10/2007 |
| JP | 2007-531509 | 11/2007 |
| JP | 2008-247803 * | 10/2008 |
| JP | 2009-173702 | 8/2009 |
| JP | 2009-263318 | 11/2009 |
| JP | 2009-274955 | 11/2009 |
| JP | 2011-503170 | 1/2011 |
| JP | 2011-512345 | 4/2011 |
| JP | 2011-524750 | 9/2011 |
| WO | 99/02548 | 1/1999 |
| WO | 2004/067568 | 8/2004 |
| WO | 2004/083257 | 9/2004 |
| WO | 2007/094248 | 8/2007 |
| WO | 2009/063427 | 5/2009 |
| WO | 2009/101194 | 8/2009 |
| WO | 2009/155180 | 12/2009 |
| WO | 2011/007885 | 1/2011 |
| WO | 2012/099216 | 7/2012 |
| WO | 2012/099224 | 7/2012 |

OTHER PUBLICATIONS

Takahashi et al., "Beautiful Skin Action of Proteoglycan from Salmon Nasal Cartilage", Food Processing & Ingredients, Jul. 1, 2010, vol. 45, No. 7, pp. 77-79.
Guo Bin et al., "Isolation, purification, and biological activities of ray cartilage glycosaminoglycans", Chinese Traditional and Herbal Drugs, vol. 37, No. 8, 2006, pp. 1210-1214 (with English abstract).
International Search Report issued Mar. 19, 2012 and English translation of International Preliminary Report on Patentability in International (PCT) Application No. PCT/JP2012/051120.
Kralovec et al., "Immunomodulating principles from shark cartilage Part 1. Isolation and biological assessment in vitro", International Immunopharmacology, vol. 3, 2003, pp. 657-669.
Yoji Kato, "Proteoglycan Gan'yu Kinosei Shokuhin no Shohinka eno Kaihatsu Kenkyu", Food Processing and Ingredients, vol. 44, No. 12, 2009, pp. 75-76, cited in ISR.
U.S. Appl. No. 13/980,415, filed Jul. 18, 2013, Kato.
U.S. Appl. No. 13/980,429, filed Jul. 18, 2013, Kato.
U.S. Office Action dated Jul. 1, 2014 issued in related U.S. Appl. No. 13/980,415.
Fujita et al., "Demonstration of EGF-like activity in salmon cartilage proteoglycan", Poster Presentation 2P-0051.
Takahashi, "Sake Binankotsu Proteoglycan no Kansetsutsu Oyobi Nankotsu Taisha ni Taisuru Yuyosei", Food Style 21, vol. 15, No. 10, 2011, pp. 52-54, cited in ISR.
Kakizaki et al., "Identification of proteoglycan from salmon nasal cartilage", Archives of Biochemistry and Biophysics, vol. 506, No. 1, Nov. 5, 2010, pp. 58-65.
Sugawara et al., "Sake Binankotsu Yurai Proteoglycan Natrium no Hinshitsu Hoji Gijutsu no Kaihatsu (Minkan To Kyodo Kenkyuhi)", Hokkai Doritsu Kushiro Suisan Shikenjo Jigyo Hokokusho, vol. 2003, 2005, p. 106, cited in ISR.
International Search Report issued Aug. 20, 2013, in International (PCT) Application No. PCT/JP2013/070134.
US Office Action dated Jan. 15, 2015 issued in U.S. Appl. No. 13/980,429.
Supplementary European Search Report dated Oct. 20, 2014 issued in European Patent Application No. 12737027.8.
Goto et al., "Anti-aging effects of high molecular weight proteoglycan from salmon nasal cartilage in hairless mice", International Journal of Molecular Medicine, vol. 29, No. 5, May 2012, pp. 761-768.
Goto et al., "Anti-aging effects of extracts prepared from salmon nasal cartilage in hairless mice", Molecular Medicine Reports, vol. 4, May 23, 2013, pp. 779-784.
Roth et al., "Intra-articular injections of high-molecular-weight hyaluronic acid have biphasic effects on joint inflammation and destruction in rat antigen-induce arthritis", Arthritis Research & Therapy, vol. 7, No. 3, Mar. 31, 2005, pp. R677-R686.
U.S. Office Action dated Jul. 10, 2015, issued in related U.S. Appl. No. 13/980,429.
Nagatsuka et al., "Radical scavenging activity of 'Nikogori' gelatin gel food made from head, bone, skin, tail and scales of fishes measured using the chemiluminescence method", International Journal of Molecular Medicine, 2007, vol. 20, pp. 843-847.
Extended European Search Report dated Oct. 14, 2015, issued in European Patent Application No. 13823573.4.
Hiroshi Sashinami, et al., "Salmon cartilage proteoglycan modulates cytokine responses to *Escherichia coli* in mouse macrophages", Biochemical and Biophysical Research Communications, 2006, vol. 351, No. 4, pp. 1005-1010.
Toshihito Mitsui, et al., "Salmon cartilage proteoglycan suppresses mouse experimental colitis through induction of Foxp3+ regulatory T cells", Biochemical and Biophysical Research Communications, 2010, vol. 402, No. 2, pp. 209-215.
Sayuri Yoshimura, et al., "Attention of Collagen-Induced Arthritis in Mice by Salmon Proteoglycan", BioMed Research International, 2014, vol. 171, No. 11, pp. 6173-6179.
Yota Tatara, et al., "Epiphycan from salmon nasal cartilage is a novel type of large leucine-rich proteoglycan", Glycobiology, 2013, vol. 23, No. 8, pp. 993-1003.
S. Nuka, et al., "Phenotypic characterization of epiphycan-deficient and epiphycan/biglycan double-deficient mice", Osteoarthritis and Cartilage, 2010, vol. 18, No. 1, pp. 88-96.
U.S. Office Action dated Jun. 4, 2015, issued in U.S Appl. No. 13/980,415.
Toshihito Mitsui, et al., "Salmon cartilage proteoglycan suppresses mouse experimental colitis through induction of Foxp3+regulatory T cells", Biochemical and Biophysical Research Communications, 2010, 402(2), pp. 209-215.
Japanese Office Action dated Jan. 4, 2017, issued in corresponding Japanese Patent Application No. 2014-526987.

* cited by examiner

PROTEOGLYCAN-CONTAINING MATERIAL

TECHNICAL FIELD

The present invention relates to a proteoglycan-containing material. More specifically, the present invention relates to a proteoglycan-containing material obtained from fish cartilage.

BACKGROUND ART

Proteoglycan is one of the major biological macromolecules for forming the substrate of the extracellular matrix of connective tissue, as with collagen, etc. Proteoglycan was hitherto obtained by being extracted and isolated from mammal cartilage (in particular, bovine cartilage). However, since the onset of bovine spongiform encephalopathy (BSE) was reported, there has been a need for an alternative source of proteoglycan, and a production method therefor.

As an alternative source for proteoglycan, aquatic animal tissue is attracting attention. Therefore, there have been attempts to extract proteoglycan from cartilage of aquatic animals, such as whales or sharks. However, due to harvest restrictions placed on these aquatic animals, it has been difficult to produce a large amount of proteoglycan. Moreover, the extraction and isolation of proteoglycan is complicated, and the solvents used for extraction have certain levels of toxicity. Therefore, the usage of proteoglycan products is limited, and they were difficulties in using them as materials of foodstuff or cosmetics.

Under such circumstances, there has been active research into various proteoglycan production methods. For example, Patent Document 1 discloses a method for purifying proteoglycan. In this method, salmon nasal cartilage is pulverized and defatted to obtain defatted dry powder, which is then subjected to extraction using a solvent. The obtained coarse extract is isolated and purified, followed by dialysis. However, this method uses an organic solvent having a certain level of toxicity, such as chloroform or methanol. Another problem of this method is that a fishy smell remains on the resulting proteoglycan.

Patent Document 2 discloses a method for purifying proteoglycan from salmon nasal cartilage using an acetic acid as an extraction solvent. Further, Patent Document 3 suggests a capability to proliferate fibroblasts, and an effect of promoting hyaluronic acid synthesis of the proteoglycan produced by the method of Patent Document 2.

As explained above, there is still ongoing research into the production, usage, and effects of proteoglycan.

CITATION LIST

Patent Documents

[Patent Document 1] Japanese Unexamined Patent Publication No. 2001-172296
[Patent Document 2] Japanese Unexamined Patent Publication No. 2002-069097
[Patent Document 3] Japanese Unexamined Patent Publication No. 2008-247803

SUMMARY OF INVENTION

Technical Problem

An object of the present invention is to produce a novel proteoglycan-containing composition (proteoglycan-containing material) from fish cartilage using a less-toxic solvent; and to find a novel usage and a superior effect of the proteoglycan-containing material.

Solution to Problem

Surprisingly, the inventors of the present invention found that an extract containing an acidic saccharide component, which was obtained by being extracted from fish cartilage using a particular method, contained proteoglycan having a greater molecular weight than that of the hitherto-known proteoglycan. Moreover, the inventors further found that the aforementioned extract had various superior effects. After several attempts to further improve the extract, the inventors completed the present invention.

In the present specification, acidic saccharide and a compound containing acidic saccharide as an ingredient are referred to as an acidic saccharide component. Since proteoglycan has a structure in which acidic saccharide and protein are bonded, proteoglycan corresponds to the acidic saccharide component; more specifically, proteoglycan is a kind of acidic saccharide component. The proteoglycan-containing material of the present invention comprises proteoglycan and acidic saccharide as acidic saccharide components. Thus, the proteoglycan-containing material of the present invention may also be referred to as an acidic saccharide-containing composition.

The present invention includes, for example, the proteoglycan-containing materials and the compositions containing proteoglycan-containing materials as set forth in the following Items.

[Item 1]
A proteoglycan-containing material comprising proteoglycan and acidic saccharide as acidic saccharide components obtained from fish cartilage, wherein the proteoglycan-containing material comprises an acidic saccharide component having a molecular weight of not less than 2000 kDa.

[Item 2]
The proteoglycan-containing material according to Item 1, wherein the proteoglycan-containing material comprises an acidic saccharide component having a molecular weight of not less than 5000 kDa.

[Item 3]
The proteoglycan-containing material according to Item 1 or 2, wherein 50 mass % or more of acidic saccharide components have a molecular weight of not less than 2000 kDa.

[Item 4]
The proteoglycan-containing material according to any one of Items 1 to 3, wherein 20 mass % or more of acidic saccharide components have a molecular weight of not less than 10000 kDa.

[Item 5]
The proteoglycan-containing material according to any one of Items 1 to 4, wherein 20 mass % or more of acidic saccharide components is proteoglycan.

[Item 6]
A food or beverage composition comprising the proteoglycan-containing material according to any one of Items 1 to 5.

[Item 7]
An oral composition comprising the proteoglycan-containing material according to any one of Items 1 to 5.

[Item 8]

A cosmetic composition comprising the proteoglycan-containing material according to any one of Items 1 to 5.

Advantageous Effects of Invention

The proteoglycan-containing material of the present invention provides various advantageous effects for skin-moisturizing and anti-aging, including an excellent skin fibroblast proliferation effect, an effect of enhancing and Improving the skin barrier function, an effect of enhancing and Improving the skin's capability to produce collagen, a dermis-thickening inhibition effect, and the like.

Schematic views showing a procedure of determining a peak area showing the proteoglycan of the present invention.

FIG. 2

Graphs showing results of quantitative analysis with respect to the amounts of acidic saccharide and protein contained in each of a plurality of 1 mL eluted fractions obtained from the samples derived from salmon nasal cartilage powder (the left graph) and a water extract of salmon nasal cartilage powder (the right graph) through gel filtration chromatography (Sepharose CL-2B packed column was used). The quantitative analysis was performed according to the carbazole-sulfuric acid method and UV absorption method.

FIG. 3

Graphs showing results of quantitative analysis with respect to the amount of acidic saccharide contained in each of a plurality of eluted fractions obtained from commercially available proteoglycan (PG-K) and commercially available glycosaminoglycan (PG-M; commercially available as chondroitin) through gel filtration chromatography. The left graph shows the results of PG-M, and the right graph shows the results of PG-K.

FIG. 4

Graphs showing results of quantitative analysis with respect to the amount of saccharide (i.e., amount of dextran) contained in each of a plurality of eluted fractions obtained from dextran molecular weight markers through gel filtration chromatography. The quantitative analysis was performed by a phenol-sulfuric acid method.

FIG. 5

Figure 4:
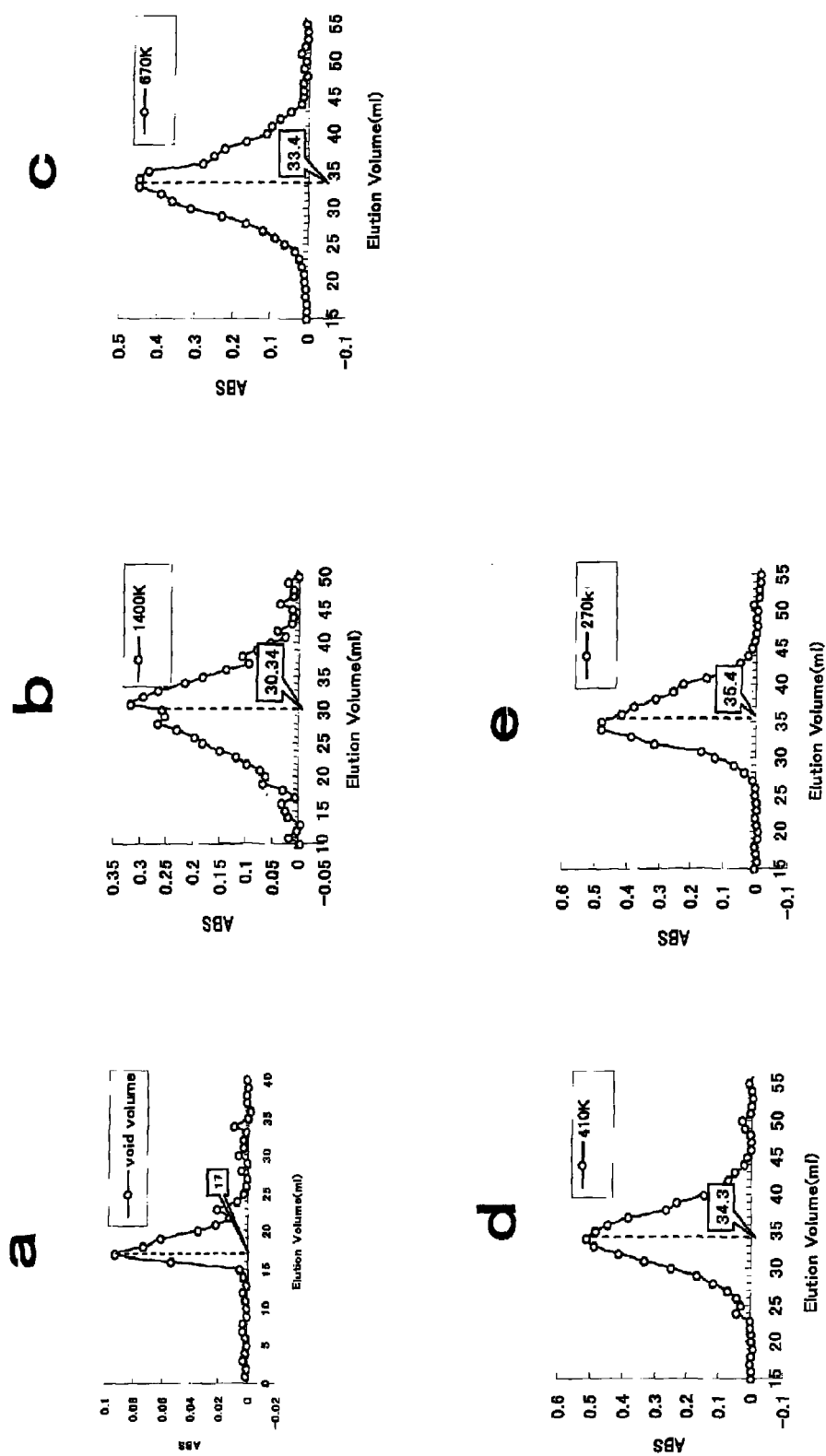

A graph showing an analytical curve based on the liquid amount at which each molecular weight marker is eluted, according to the results of FIG. 4.

FIG. 6

Figure 1:
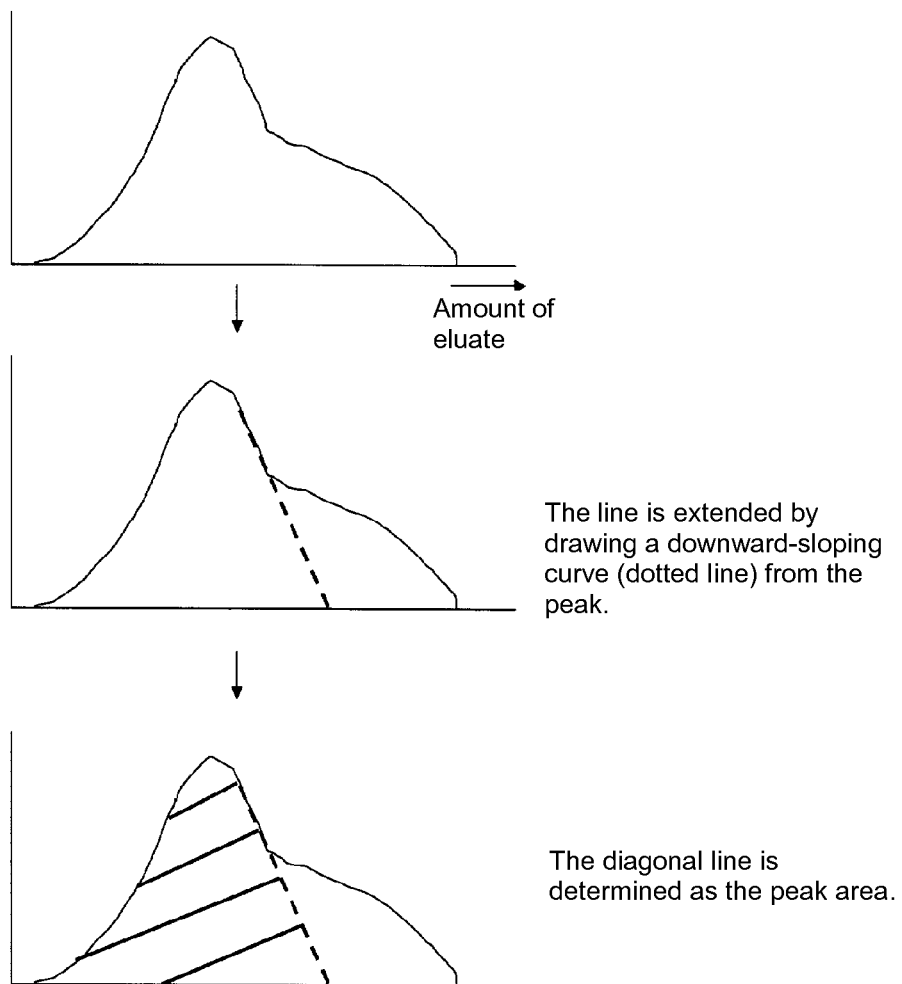
FIG. 1
Figure 2:
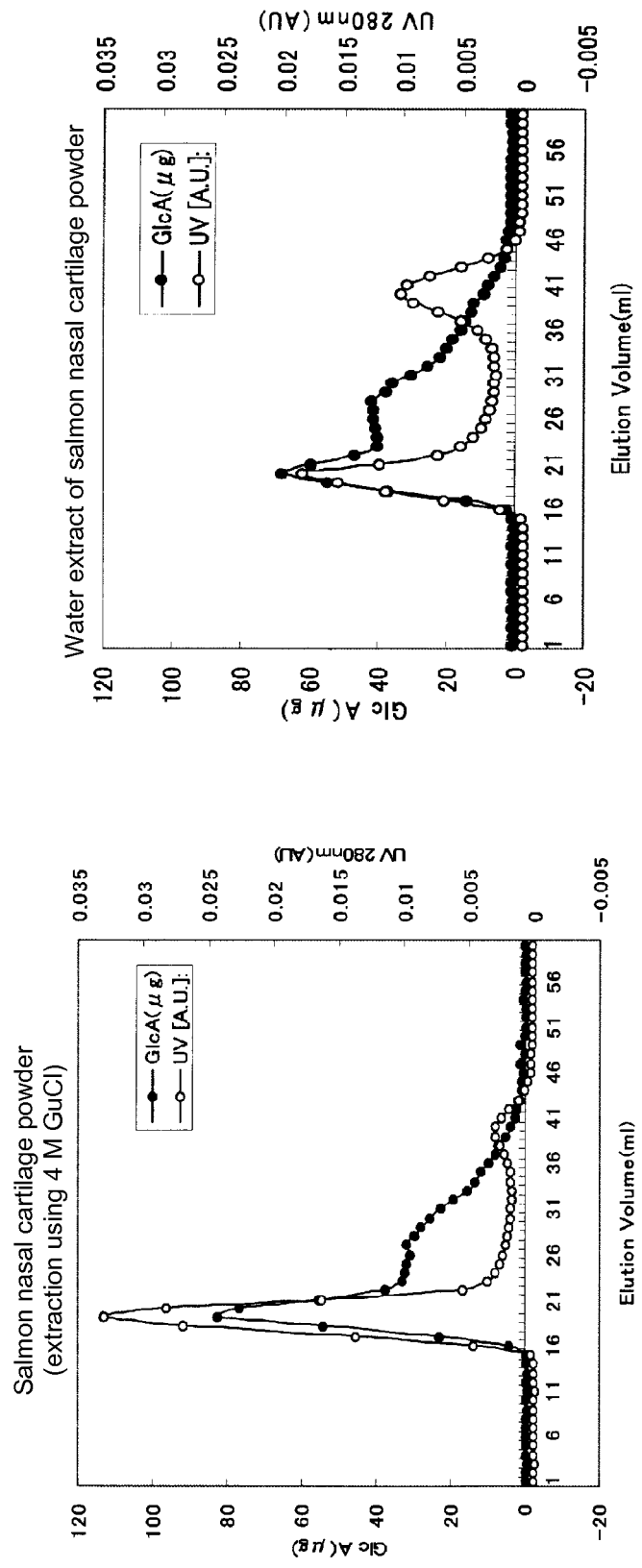

A graph that summarizes measurement results of acidic saccharide amounts shown in FIG. 1 and FIG. 2.

FIG. 7

A graph showing quantitative analysis with respect to the amount of acidic saccharide contained in each of a plurality of 1 mL eluted fractions obtained from the samples derived from salmon nasal cartilage powder through gel filtration chromatography (Sephacryl S-1000 SF packed column was used). The quantitative analysis was performed by the carbazole-sulfuric acid method.

FIG. 8

A graph showing analysis of capabilities to proliferate human skin fibroblasts of salmon nasal cartilage powder and a water extract of salmon nasal cartilage powder.

FIG. 9

A graph showing analysis of an influence on the skin barrier function (TEWL value) by oral administration of salmon nasal cartilage powder and a water extract of salmon nasal cartilage powder.

FIG. 10

A graph showing analysis of an influence on the skin elasticity by oral administration of salmon nasal cartilage powder and a water extract of salmon nasal cartilage powder.

FIG. 11

A graph showing analysis of an influence on capability to produce collagen by oral administration of salmon nasal cartilage powder, and a water extract of salmon nasal cartilage powder.

FIG. 12

A graph showing measurements of back dermis thickness of mice orally administered with salmon nasal cartilage powder, and a water extract of salmon nasal cartilage powder, for analysis of an influence on dermis-thickening by these substances.

FIG. 13

A graph showing analysis of an influence on the skin barrier function (TEWL value) by transdermal administration of salmon nasal cartilage powder and a water extract of salmon nasal cartilage powder.

FIG. 14

A procedure of fractionation of a water extract of salmon nasal cartilage powder by way of ion-exchange chromatography and gel filtration chromatography.

FIG. 15

A graph showing analysis of cell proliferation effect of each fraction of a water extract of salmon nasal cartilage powder; specifically, a graph showing the cell number of each fraction 7 days after the addition of each sample (50 μg/ml). "PGNP water extract" is a water extract of salmon nasal cartilage powder.

FIG. 16

A graph showing analysis of cell proliferation effect of each fraction of a water extract of salmon nasal cartilage powder; specifically, a graph showing the cell number of each fraction 7 days after the addition of each sample (10 μg/ml).

DESCRIPTION OF EMBODIMENTS

The present invention is more specifically described below. In the following, the molecular weights and the mean molecular weights of acidic saccharide and proteoglycan are based on the measurement values obtained in gel filtration chromatography using dextran as a molecular weight marker.

The proteoglycan-containing material of the present invention is produced from fish cartilage. Examples of fish include, but are not limited to, trout (humpback salmon, cherry salmon, satsukimasu salmon, etc.), salmons (chum salmon, sockeye salmon, silver salmon, chinook salmon, steelhead, etc.), sharks, and cods. Oncorhynchus (salmonidae), in particular, salmons and trout, are preferable. The cartilage to be used is also not limited; however, head cartilage, in particular nasal cartilage, is preferable. Moreover, since fish heads are usually discarded when fish is processed into foodstuff, the cost of fish heads is low, and a large amount of fish head can be stably supplied.

In the present invention, "acidic saccharide component" designates acidic saccharide or a compound containing acidic saccharide as an ingredient. The proteoglycan-containing material of the present invention contains an acidic saccharide component (i.e., acidic saccharide or a component containing acidic saccharide as an ingredient).

Here, "acidic saccharide" is a polysaccharide containing an uronic acid. Examples of acidic saccharide contained in the proteoglycan-containing material of the present invention include glycosaminoglycans such as hyaluronic acid, chondroitin and the like. Except for hyaluronic acid, glycosaminoglycan is generally present by being covalently bonded with protein (i.e., as proteoglycan).

A specific example of the compound containing acidic saccharide as an ingredient is proteoglycan. Proteoglycan has a structure in which glycosaminoglycan and protein are covalently bonded. Glycosaminoglycan that forms proteoglycan is acidic saccharide consisting of a repeating sulfated disaccharide unit. Specifically, examples thereof include chondroitin sulfate, dermatan sulfate, and heparan sulfate. That is, proteoglycan is a compound having a structure in which protein and acidic saccharide are bonded.

In the repeating disaccharide structure of the acidic saccharide component, generally, one of the disaccharides is amino sugar, and the other is an uronic acid. Therefore, the detection of acidic saccharide components may be performed using a carbazole-sulfuric acid method, which is one of the ordinary methods for detecting uronic acids.

The carbazole-sulfuric acid method is performed by adding a carbazole solution, which is a color component of glucuronic acid (Glc A) and iduronic acid, i.e., uronic acid, to a measurement specimen, measuring the absorbency using a spectrophotometer, and plotting an analytical curve using the glucuronic acid standard solution having a specific concentration, thereby finding a glucuronic acid content in the specimen. More specifically, the carbazole-sulfuric acid method can be performed as follows.

2.5 ml of a reagent obtained by dissolving 0.95 g of sodium borate decahydrate in 100 ml of a concentrated sulfuric acid is placed in a test tube, and ice-cooled. 0.5 ml of a test object (containing 4 to 40 µg of uronic acid) is gently layered thereon. The mixture is well-stirred while being ice-cooled, thereby keeping it at room temperature or below. After the test tube is covered with a glass ball lid, the test tube is heated in a boiling water bath for 10 minutes, followed by water-cooling to decrease the temperature to room temperature. Then, 0.1 ml of a reagent obtained by dissolving 125 mg of carbazole in 100 ml of anhydrous methyl alcohol is added and mixed therewith, and the mixture is heated in a boiling water bath for 15 minutes. Thereafter, the mixture is water-cooled to room temperature, and an absorbency at 530 nm is measured. In the blank test, 0.5 ml of distilled water is used. Simultaneously, an analytical curve is plotted using a glucuronic acid.

The mean molecular weight of the acidic saccharide component contained in the proteoglycan-containing material of the present invention is generally about 2000 kDa to 40000 kDa, preferably 2500 kDa to 30000 kDa, more preferably 3000 kDa to 20000 kDa, further preferably 3000 kDa to 10000 kDa, and further more preferably 4000 kDa to 8000 kDa.

The proteoglycan-containing material of the present invention contains an acidic saccharide component having a molecular weight of not less than 2000 kDa, preferably not less than 2500 kDa, more preferably not less than 3000 kDa, further preferably not less than 4000 kDa, and further more preferably not less than 5000 kDa.

The proportion of an acidic saccharide component having a molecular weight of not less than 2000 kDa in the proteoglycan-containing material of the present invention is preferably not less than 50 mass %, more preferably not less than 55 mass %, further preferably not less than 60 mass %, and still further more preferably not less than 65 mass %.

The proteoglycan contained in the proteoglycan-containing material of the present invention has a significantly greater molecular weight (MW) than the hitherto-available proteoglycan. More specifically, even a small proteoglycan in the proteoglycan-containing material of the present invention has a molecular weight of at least about 5000 kDa to 6000 kDa or more. Thus, the proteoglycan-containing material of the present invention contains proteoglycan having a molecular weight of about 5000 kDa or more. For example, the proteoglycan-containing material of the present invention contains proteoglycan having a molecular amount of about 5000 kDa to 100000 kDa, preferably 5000 kDa to 90000 kDa, more preferably 5000 kDa to 80000 kDa, further more preferably 5000 kDa to 70000 kDa. Moreover, although the mean molecular weight of the proteoglycan contained in the proteoglycan-containing material of the present invention is not particularly limited, the mean molecular weight is generally about 6000 kDa to 60000 kDa, preferably about 7000 kDa to 50000 kDa, more preferably about 9000 kDa to 40000 kDa.

The proportion of the proteoglycan having a molecular weight of 6000 kDa or more (further preferably 10000 kDa or more) in the proteoglycan-containing material of the present invention is preferably not less than 20 mass % or more, more preferably not less than 30 mass %.

The proteoglycan-containing material of the present invention preferably contains an acidic saccharide component in an amount of, on a dry mass basis, 15 to 70 mass %, more preferably 30 to 70 mass %. Moreover, the proteoglycan-containing material of the present invention preferably contains proteoglycan in an amount of, on a dry mass basis, 4 to 40 mass %, more preferably 10 to 40 mass %, further preferably 15 to 40 mass %.

The molecular weight of the acidic saccharide component or proteoglycan contained in the proteoglycan-containing material of the present invention can be measured using chromatography or the like. In particular, the molecular weight is preferably measured by gel filtration chromatography. More specifically, for example, an agarose (agarose, cross-linked agarose, etc.) gel matrix may be used as a carrier of the column, and a phosphate buffer (preferably containing sodium chloride) may be used as a buffer. Through the gel filtration of the proteoglycan-containing material, the molecular weight of the acidic saccharide component or proteoglycan contained in the composition can be determined according to the elution volume before elution of the acidic saccharide component or proteoglycan.

Because proteoglycan has a structure in which glycosaminoglycan (mucopolysaccharide) and protein are covalently bonded, the elution of proteoglycan in the chromatography can be detected by monitoring the acidic saccharide and protein. More specifically, a chromatogram obtained by monitoring of acidic saccharide and a chromatogram obtained by monitoring protein are overlaid to confirm whether there is an overlapped peak in substantially the same eluate range in the two chromatograms. If such a peak is found, the peak is regarded as the detection of proteoglycan. For example, the carbazole-sulfuric acid method can be used for monitoring acidic saccharide. The eluted fraction of chromatography is divided into separate fractions of a predetermined amount, and the acidic saccharide amount contained in each fraction is determined using the carbazole-sulfuric acid method. Further, for example, the monitoring of protein can be performed according to the UV absorption method (in which protein quantity is determined by measuring absorbencies of tryptophan, tyrosine, and phenylalanine having absorptions in the vicinity of 280 nm), ninhydrin reaction, BCA method, Bradford method, Lowry method, biuret method, and the like. Among these, quantitative analysis using the UV absorption method is easily done.

Further, the molecular weight can be determined from the amount of eluate, as follows. A molecular weight marker is subjected to gel filtration chromatography in the same manner, and the liquid measure at which the molecular weight marker is eluted is measured to plot an analytical curve (elute amount vs. molecular weight). A suitable molecular weight marker is appropriately selected and purchased in consideration of the molecular weight of the proteoglycan-containing material or the type of gel matrix to be used. For example, a molecular weight marker made of dextran can be used. Such a molecular weight marker may be purchased from Sigma-Aldrich Co., etc.

In addition to the acidic saccharide component, the proteoglycan-containing material of the present invention also contains other fish cartilage-derived components. Examples thereof include proteins such as collagen, and salts.

In the present invention, the mean molecular weight of a substance designates a specific molecular weight determined as follows. A line (bisector) perpendicular to the horizontal axis (amount of eluate) that divides the peak area in the chromatogram of the substance obtained by analysis using gel filtration chromatography is drawn, and a mean molecular weight is determined from the amount of eluate corresponding to the position of the bisector, using an analytical curve. More specifically, the mean molecular weight of a substance designates a molecular weight determined according to the method disclosed in the "Analysis of Molecular Weight of Proteoglycan-Containing Materials" section of the Examples.

For example, the mean molecular weight of the acidic saccharide component contained in the proteoglycan-containing material is found by isolating the proteoglycan-containing material by gel filtration chromatography, drawing a line that divides the area of the chromatogram obtained by monitoring the acidic saccharide component contained therein, and finding the mean molecular weight by determining a molecular weight from the amount of eluate corresponding to the position of the bisector using an analytical curve (in other words, by substituting the amount of eluate in the equation of the analytical curve). The monitoring of the acidic saccharide component is more specifically described below. The proteoglycan-containing material is subjected to gel filtration chromatography analysis, followed by elution at a predetermined speed, and the resulting eluate is divided into separate fractions of a predetermined amount. The fractions are subjected to quantitative analysis, and the measured amount of acidic saccharide in each eluate (fraction) is plotted to create a chromatogram.

Further, the mean molecular weight of proteoglycan contained in the proteoglycan-containing material is found by drawing a line that divides the peak area denoting proteoglycan in a chromatogram obtained by gel filtration chromatography analysis of the proteoglycan-containing material, and finding the mean molecular weight by determining a molecular weight from the amount of eluate corresponding to the position of the bisector using an analytical curve.

As described above, the peak denoting proteoglycan corresponds to a peak that is substantially overlapped when a chromatogram obtained by the monitoring of acidic saccharide and a chromatogram obtained by monitoring protein are overlaid.

If the rise and the fall of the peak denoting proteoglycan cannot be specified because they overlap with the peaks of other acidic saccharide components, the rise and the fall are estimated based on the shape of the peak. Using the estimated values of the rise and the fall, the molecular weight and the mean molecular weight are found. FIG. 1 shows an example of such an estimation. FIG. 1 is a schematic view showing a method for estimating the peak shape when the fall of the peak cannot be specified. In FIG. 1, the line is extended by drawing a downward-sloping curve, thereby determining the peak shape.

For both an acidic saccharide component and proteoglycan, the molecular weight or mean molecular weight is preferably found by analyzing a chromatogram obtained by monitoring the acidic saccharide.

Moreover, by collecting only the fraction corresponding to the peak denoting proteoglycan during the gel filtration chromatography, it is possible to purify proteoglycan contained in the proteoglycan-containing material of the present invention. Further, by collecting from the initial fraction to the fraction corresponding to the peak denoting proteoglycan, it is possible to obtain a proteoglycan-containing material having a further greater mean molecular weight.

The proportion of proteoglycan in the acidic saccharide component contained in proteoglycan-containing material of the present invention is generally not less than 20 mass %, preferably 20 to 60 mass %, more preferably 25 to 55 mass %, further preferably 30 to 50 mass %. The proportion of proteoglycan in the acidic saccharide component can be found from the chromatogram used to find the molecular weight of the acidic saccharide component or proteoglycan. More specifically, by finding the proportion of the peak area showing proteoglycan among the entire area of the chromatogram obtained by monitoring the acidic saccharide component of the proteoglycan-containing material, it is possible to find the proportion of proteoglycan in the acidic saccharide component.

As described above, the proteoglycan-containing material of the present invention is produced from fish cartilage. More specifically, the proteoglycan-containing material of the present invention can be produced by defatting fish cartilage using ethanol. Further, the proteoglycan-containing material may be produced by being extracted from the defatted fish cartilage through water extraction.

For example, the proteoglycan-containing material is produced through the following steps.

Step (1): Water Treatment Step

Fish tissue containing cartilage (e.g., a fish head) is Immersed in water for several minutes to several days at room temperature or a low temperature (about 0 to 40° C.). The tissue may be allowed to stand still in water, stirred during immersion, stirred together with water using a line mixer, etc. The amount of water is not particularly limited; however, it is preferable to use a sufficient amount of water so that all of the tissue containing cartilage is immersed therein. Such complete immersion of the tissue removes the fishy smell from the tissue, and enables easy removal of the parts other than cartilage because the tissue is swollen by the infiltration of the water. Before the immersion in water, it is possible to slice or crack the tissue containing cartilage beforehand, or to separate removable parts from the tissue other than cartilage.

When the tissue is deodorized and desirably swollen by sufficient immersion in water, lipids, etc., are extracted from fish tissue containing cartilage (that is, the tissue containing cartilage is defatted). The extracted lipids are dissolved or suspended in the water layer, or floats in the water layer as a lipid layer. By removing the water layer and the lipid layer, the lipids contained in the tissue containing cartilage are removed. It is also possible to remove these unwanted substances by centrifugation.

Step (2): Ethanol Treatment Step

After removing the lipid layer and the water layer, the resulting residue (cartilage tissue) is isolated. Ethanol is added to the residue, and the lipids are further removed by extraction. By further removing lipids, it is possible to more reliably remove odor. Hydrous ethanol may also be used. Further, it is preferable to pulverize the residue (cartilage tissue) before addition of the organic solvent. The method for pulverizing the tissue is not limited. For example, the pulverization may be performed using a device capable of finely pulverizing cartilage materials, such as a ball mill, swing mill, low-temperature-grinder, freezing grinder, rotor mill, grind mix, mixer mill, and the like. The particle size of the pulverized tissue is preferably, but not limited to, about 10 to 500 μm, more preferably about 50 to 250 μm. The particle size can be measured according to the laser diffraction scattering method.

For example, this step may be performed by immersing the cartilage tissue (preferably, pulverized cartilage tissue) obtained above in ethanol in a sufficient amount to fully immerse the tissue; stirring the immersed tissue, or allowing it to stand still; and then removing the solvent. The immersion is preferably performed a plurality of times (e.g., 2 to 5 times). It is also possible to remove lipids by circulating ethanol. This process is more preferably performed with the Soxhlet extractor or the like. After such a treatment, solids are separated. The collected solids may be dried by air-drying or the like to completely remove the organic solvent.

The solids thus obtained are used as a proteoglycan-containing material.

A more detailed example of Step (2) above may be the following method comprising the Steps [1] to [9].

[1] Extraneous tissue such as skin or bone is removed from salmon nasal cartilage, and the resulting cartilage is pulverized with a meat chopper.
[2] Tap water or purified water having a pH of 6 to 7.5 in an amount that is equal or double the amount (volume) of the cartilage is added to the pulverized salmon nasal cartilage, and the mixture is sufficiently stirred at 40° C. or below.
[3] After stirring, the mixture is subjected to centrifugation using a centrifuge to collect solids.
[4] Steps [2] and [3] are performed once or twice.
[5] The resulting solids are further finely pulverized with a wet grinder.
[6] Ethanol having a purity of 95% or more in an amount (volume) that is about ten times the amount of cartilage is added to the finely pulverized salmon nasal cartilage about, and the mixture is sufficiently stirred at 40° C. or below.
[7] After stirring, the mixture is subjected to centrifugation using a centrifuge to collect solids.
[8] Steps [6] and [7] are performed 1 to 3 times.
[9] The solids are dried, as necessary.
In Step [5], fine pulverization may be performed after the resulting solids are freeze-dried.

Step (3): Water Extraction Step

As the proteoglycan-containing material of the present invention, it is more preferable to use an extract resulting from additional water extraction. Therefore, the solids obtained in Step (2) are preferably further subjected to water extraction. For example, the solids obtained in Step (2) are immersed in a sufficient amount of water to be completely immersed therein, the mixture is stirred, and insoluble matter is removed. In this manner, the obtained solution or a dried product thereof is used as a proteoglycan-containing material. The pH of the water to be added is generally 5.5 to 8.0, preferably 6.0 to 7.5, more preferably 6.5 to 7.5. More specifically, for example, the tissue is stirred while immersed in water for about 30 minutes to 6 hours, or stirred together with water using a line mixer or the like; and insoluble matter is removed. After removing the insoluble matter, it is possible to perform drying by a usual method. Further, it is also possible to add ethanol in a double to tenfold amount (volume) after removing the insoluble matter, thereby collecting the resulting solids. In this case, sodium chloride may be added before the addition of ethanol.

A more detailed example of Step (3) above may be the following method comprising Steps [10] to [12], which are performed after Steps [1] to [9].
[10] Purified water having a pH value of 6 to 7.5 in an amount (volume) that is approximately equal or double that of the dried product obtained in Step [9] is added to the dried product, and the mixture is sufficiently stirred at 40° C. or lower for about 30 minutes to 48 hours.
[11] Centrifugation is performed to remove solids.
[12] The solids are dried, as necessary.

It is also possible to add ethanol after Step [11], stir the mixture, and collect the resulting solids.

As described above, the proteoglycan-containing material of the present invention may also be produced by Steps (A) and (B), or by Steps (A) to (C).
(A) A step of purifying fish cartilage
(B) A step of removing lipids from fish cartilage using an organic solvent
(C) A step of further performing water extraction with respect to defatted fish cartilage, thereby collecting an extract Steps (A), (B), and (C) correspond respectively to Steps (1), (2), and (3) described above.

The proteoglycan-containing material of the present invention may be suitably used for skin anti-aging. Skin is constantly exposed to various kinds of damage. For example, in the dermic layer, the epidermis barrier function decreases due to external factors (for example, optical radiation such as ultraviolet) or internal factors (for example, aging). Such damage causes an increase in transepidermal water loss (TEWL), thereby causing dry or rough skin. Further, for the same reason, a decrease in capability to produce collagen, a decrease in skin elasticity, or dermis-thickening may occur in the dermic layer, thereby facilitating skin-hardening. This may result in wrinkles or the like.

The proteoglycan-containing material of the present invention exhibits various effects (advantageous effects in terms of skin moisturizing and anti-aging, such as skin fibroblast proliferation effect, effects of enhancing and improving the skin barrier function, effects of enhancing and improving the skin's capability to produce collagen, dermis-thickening inhibition effect, and the like) to suppress or treat such skin symptoms. In particular, the proteoglycan-containing material of the present invention is suitable to prevent or treat the aforementioned skin symptoms caused by optical radiation (in particular, ultraviolet radiation).

The usage of the proteoglycan-containing material of the present invention is not limited; however, the proteoglycan-containing material of the present invention is particularly useful for products in the oral-care industry, cosmetic industry, and food and beverage industry. Accordingly, the present invention includes oral compositions containing the proteoglycan-containing material of the present invention, cosmetic compositions containing the proteoglycan-containing material of the present invention, and food and beverage compositions containing the proteoglycan-containing material of the present invention.

The oral compositions oralcontaining the proteoglycan-containing material (these oral compositions may be hereinafter referred to as oral compositions of the present invention) used for oral-care products can be produced by appropriately combining the proteoglycan-containing material of the present invention with other components (e.g., abrasives, foaming agents, cleaners, surfactants, wetting agents, pH adjusters, thickeners, flavoring agents, and the like) generally used for oral compositions. Examples of the oral composition products include paste agents, ointments, gels, embrocations, sprays, supplements, liquids, mouthwashes, paste, chewing gums, troches, and tablets, which may be manufactured by usual methods.

Such oral compositions of the present invention can be used by being sprayed into the oral cavity, or as a mouthwash. By such applications, the oral compositions proliferate, in particular, the fibroblasts in the oral cavity, thereby enhancing and improving the skin barrier function and the capability to produce collagen. With such advantages, the oral compositions of the present invention are appropriately used for regeneration and anti-aging of oral tissue.

The amount of the acidic saccharide component contained in the proteoglycan-containing material of the oral compositions of the present invention is not particularly limited; however, the amount is generally 0.002 to 13 mass %, preferably 0.01 to 5 mass %, more preferably 0.02 to 3 mass %, based on the entire composition. Moreover, the amount of proteoglycan contained in the proteoglycan-containing material of the oral composition is also not limited; however, the amount is generally 0.001 to 5 mass %, preferably 0.005 to 2 mass %, more preferably 0.01 to 1 mass %, based on the entire composition.

The cosmetic compositions containing the proteoglycan-containing material of the present invention (these cosmetic compositions may be hereinafter referred to as cosmetic compositions of the present invention) used for cosmetic products can be produced by appropriately combining the proteoglycan-containing material of the present invention with cosmetically acceptable media, bases, carriers, or additives; and, as necessary, other cosmetically acceptable components and materials by a usual method. More specifically, examples of cosmetic compositions include emulsions, lotions, creams, serums, foundations, masks, and sunscreens, which are produced by using the proteoglycan-containing material of the present invention. Such cosmetic compositions of the present invention are preferably used for prevention or treatment of sunburn, moisturizing and anti-aging of the skin (e.g., prevention or treatment of dry skin, rough skin, facial wrinkles or sagging skin), and the like.

The amount of the acidic saccharide component contained in the proteoglycan-containing material of the cosmetic composition of the present invention is not particularly limited; however, the amount is generally 0.002 to 5 mass %, preferably 0.02 to 2 mass %, more preferably 0.1 to 2 mass %, based on the entire composition. Moreover, the amount of proteoglycan contained in the proteoglycan-containing material of the cosmetic compositions is also not limited; however, the amount is generally 0.001 to 2 mass %, preferably 0.01 to 1 mass %, more preferably 0.05 to 1 mass %, based on the entire composition.

The food and beverage compositions containing the proteoglycan-containing material (these food and beverage compositions may be hereinafter referred to as food and beverage compositions of the present invention) used for food and beverage products can be produced by appropriately combining the proteoglycan-containing material of the present invention with food-hygienically acceptable bases, carriers, or additives; and, as necessary, other components or materials used for food and beverages. Examples thereof include fabricated food or beverages with claimed effects of moisturizing and anti-aging of the skin (e.g., prevention or treatment of dry skin, rough skin, facial wrinkles or sagging skin), food with health claims (food with nutrient function claims, food for specified health uses, etc.), supplements, weight-reducing food, food for patients, etc., which contain the proteoglycan-containing material of the present invention. Moreover, the present invention also includes moisturizers and skin anti-aging agents formed of the aforementioned food and beverage compositions of the present invention. The moisturizers and skin anti-aging agents may be supplied in the forms of drinks, tablets, capsules, granules, jelly, troches, or the like for cosmetic or skin anti-aging purposes (e.g., prevention or treatment of dry skin, rough skin, facial wrinkles or sagging skin).

The amount of the acidic saccharide component contained in the proteoglycan-containing material of the food and beverage compositions of the present invention is not particularly limited; however, in the case of a food composition or an agent comprising a food composition, the amount is generally 0.01 to 50 mass %, preferably 0.02 to 25 mass %, more preferably 0.1 to 8 mass %, based on the entire composition or agent. The amount of the acidic saccharide component contained in the proteoglycan-containing material of a beverage composition or an agent comprising a beverage composition is generally 0.002 to 13 mass %, preferably 0.01 to 8 mass %, more preferably 0.1 to 2 mass %, based on the entire composition or agent. Moreover, the amount of proteoglycan contained in the proteoglycan-containing material of the food and beverage compositions is also not limited; however, in the case of a food composition or an agent comprising a food composition, the amount is generally 0.005 to 20 mass %, preferably 0.01 to 10 mass %, more preferably 0.05 to 3 mass %, based on the entire composition or agent. In the case of a beverage composition or an agent comprising a beverage composition, the amount is generally 0.001 to 5 mass %, preferably 0.005 to 3 mass %, more preferably 0.01 to 1 mass %, based on the entire composition or agent.

Furthermore, the proteoglycan-containing material of the present invention is preferably applied in combination with hyaluronic acid or collagen. In a combination with these substances, the effect of the proteoglycan-containing material of the present invention increases. Therefore, the aforementioned oral compositions, cosmetics compositions, and food and beverage compositions of the present invention also preferably comprise a hyaluronic acid and/or collagen (preferably collagen hydrolysate). In particular, oral administration of the proteoglycan-containing material of the present invention together with a hyaluronic acid is preferable, as it further improves the skin moisturizing and anti-aging effect. The amount of hyaluronic acid is not particular limited; however, it is 0.01 to 1 parts by mass, preferably 0.02 to 0.5 part by mass, more preferably 0.05 to 0.2 part by mass, per part by mass of the proteoglycan-containing material of the present invention.

The amount of acidic saccharide components contained in the oral compositions, cosmetic compositions, and food and beverage compositions of the present invention can be found, for example, according to the carbazole-sulfuric acid method. The amount of acidic saccharide components can also be found by acidic saccharide detection chromatograms obtained by gel filtration chromatography of those compositions. Further, the amount of proteoglycan contained in those compositions can be determined, for example, by performing gel filtration chromatography of each composition, overlaying the acidic saccharide detection chromatogram and the protein detection chromatogram, and detecting and determining the quantity of proteoglycan represented by an overlapped peak.

The present invention also includes a method for orally or transdermally applying the proteoglycan-containing material of the present invention, thereby obtaining the effects recited in this specification, i.e., the effect of proliferating fibroblasts, or the effect of enhancing or improving the skin barrier function. The method may be performed by directly using the proteoglycan-containing material of the present invention, or more preferably using the aforementioned oral compositions or the cosmetic compositions of the present invention. The subject of the method is not limited; however, it is more preferable to perform the method on a person who suffers from a decrease in skin barrier function due to aging or sunburn. The method may also be applied for cosmetic purposes. The application amount is also not limited, and any desired amount may be applied.

Furthermore, the present invention also includes a method for orally administering the proteoglycan-containing material of the present invention, thereby obtaining the effects recited in this specification, i.e., the effect of proliferating fibroblasts, the effect of enhancing or improving the skin barrier function, the effect of enhancing or improving skin elasticity, the effect of preventing dermis-thickening, or the effect of enhancing or improving the skin's capability to produce collagen. The method may be performed by directly using the proteoglycan-containing material of the present invention, or more preferably using the aforementioned food and beverage compositions of the present invention. The subject of the method is not limited; however, it is more preferable to perform the method on a person who suffers from a decrease in skin barrier function, or a decrease in skin elasticity due to aging or sunburn. The method may also be applied for cosmetic purposes. The application amount is also not limited, and any desired amount may be applied.

EXAMPLES

Hereinafter, the present invention will be described in detail. However, the present invention is not limited to the following Examples.

Production of Proteoglycan-Containing Materials

A head of salmon was immersed in water, and allowed to stand for one day to swell. Then, tissue other than nasal cartilage was removed from the head of salmon to obtain salmon nasal cartilage. The salmon nasal cartilage was crushed into salmon nasal cartilage powder. After 100 mL of water was added to 100 g of the powder and gently stirred, the mixture was allowed to stand at room temperature for 10 minutes, and defatted. Centrifugation (8000 rpm, 30 minutes, room temperature) was then carried out, and the obtained residue (salmon nasal cartilage defatted powder) was collected and freeze-dried. Using an ultracentrifugal mill, 9.02 g of the freeze-dried salmon nasal cartilage defatted powder was pulverized into fine powder with a particle size of about 100 to 200 μm (measured by the laser diffraction scattering method). The fine powder was washed with 20 mL of ethanol three times, and then air-dried to obtain 7.69 g of fine powder containing acidic saccharide components. This fine powder may be hereinafter referred to as "salmon nasal cartilage powder." Note that "wash" with ethanol here means an operation (ethanol precipitation) in which fine powder is dispersed in ethanol, and then subjected to centrifugation to collect the precipitate.

Furthermore, after 1000 mL of purified water at room temperature (pH 6.5) was added to 20 g of salmon nasal cartilage powder and stirred for 30 minutes, the mixture was allowed to stand at room temperature for 10 minutes. This was followed by centrifugation (8000 rpm, 30 minutes, room temperature). The supernatant was collected and dried by concentration to obtain about 7 g of powder containing acidic saccharide components. The water extract thus obtained may be hereinafter referred to as "water extract of salmon nasal cartilage powder."

The salmon nasal cartilage powder contained about 20 mass % of acidic saccharide components and about 9 mass % of proteoglycan (that is, about 11 mass % of acidic saccharide such as glycosaminoglycan was contained therein). Additionally, the water extract of salmon nasal cartilage powder contained about 35 mass % of acidic saccharide components and about 15 mass % of proteoglycan (that is, about 20 mass % of acidic saccharide such as glycosaminoglycan was contained therein). These percentages were calculated on the basis that uronic acid (glucuronic acid) was quantified by the carbazole-sulfuric acid method; further, the amount (mass) of chondroitin sulfate was determined using the following formula well known in this quantification method, and the amount of chondroitin sulfate was defined as the amount of acidic saccharide components.

$$\text{The amount of chondroitin sulfate} = \text{the amount of glucuronic acid} \times 2.593 \quad [\text{Formula 1}]$$

Hereinafter, if not otherwise specified, the amount of acidic saccharide components determined by the carbazole-sulfuric acid method indicates the amount of chondroitin sulfate determined in the same manner as above.

In addition, the proteoglycan content can be calculated from the area ratio of the peak area showing proteoglycan in a chromatogram to the entire area of the chromatogram. The chromatogram is obtained as described below, by conducting gel filtration chromatography analysis while monitoring the amount of acidic saccharide components by quantifying uronic acid. Specifically, the proteoglycan content can be calculated by multiplying the area ratio by the amount of acidic saccharide components.

Analysis of Molecular Weight of Proteoglycan-Containing Materials

The molecular weight of the obtained proteoglycan-containing materials was analyzed by gel filtration chromatography. More specifically, salmon nasal cartilage powder and a water extract of salmon nasal cartilage powder, used as samples, were subjected to gel filtration chromatography conducted under the following conditions; and 1 mL eluted fractions were collected to quantify the amounts of acidic saccharide and protein contained in each of the fractions by the carbazole-sulfuric acid method and the UV absorption method, respectively.

FIG. 2 shows chromatograms obtained as a result of the gel filtration chromatography analysis. Note that the chromatograms that analyze the amount of acidic saccharide show the amount of glucuronic acid quantified by the carbazole-sulfuric acid method (not the amount of chondroitin sulfate determined by multiplying the amount of glucuronic acid by 2.593). With respect to the salmon nasal cartilage powder, extraction was performed with 4 M guanidine hydrochloride (4 M GuCl) to increase purity, and the resulting extract was used as a sample. The extraction was specifically carried out as follows. 4 M GuCl was added to 1 g of the salmon nasal cartilage powder and stirred at 4° C. for one day, followed by centrifugation. A threefold amount of ethanol saturated with sodium chloride was added to the supernatant, and left to stand overnight. Then, centrifugation was performed to collect the precipitate. This precipitate was used as a sample for the gel filtration chromatography. The water extract of salmon nasal cartilage powder was used as is, as a sample.

Figure 3:
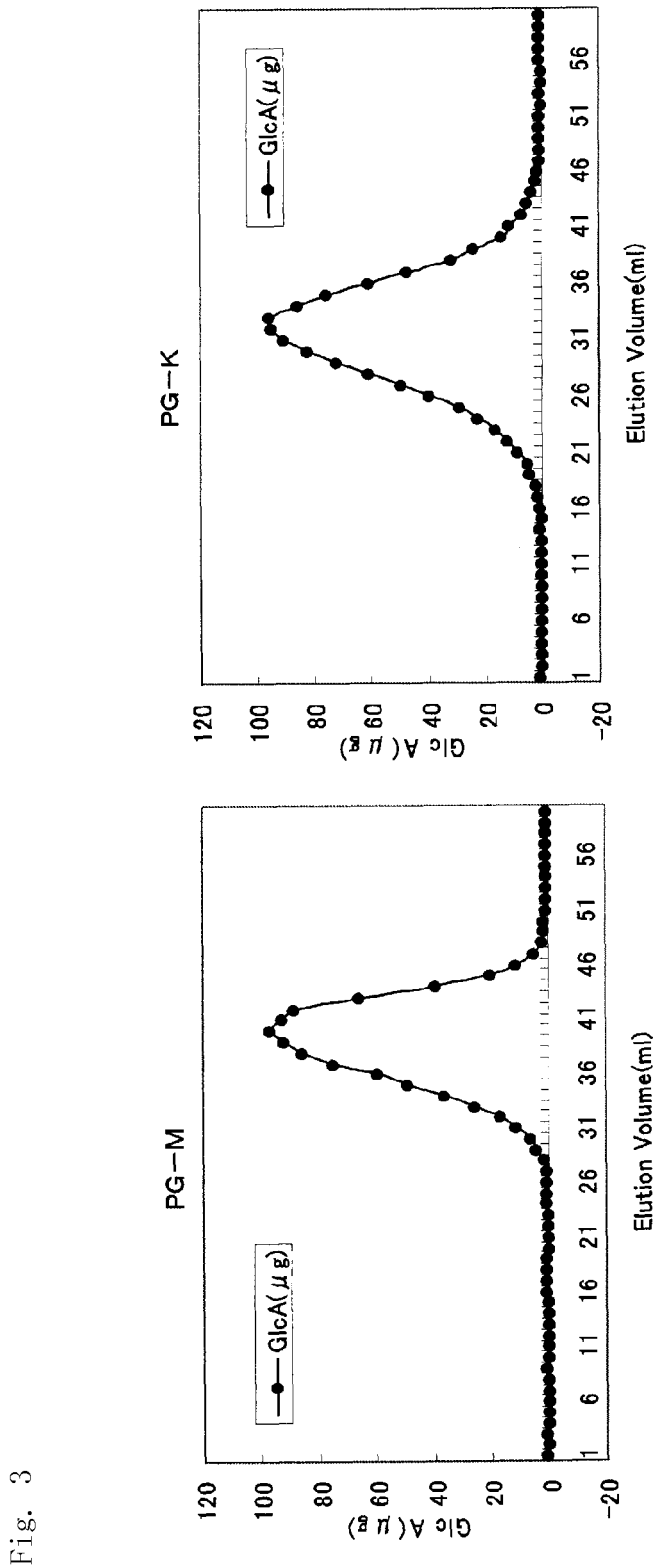

[Gel Filtration Chromatography Conditions]
Column: Sepharose CL-2B packed column (φ1 cm×48 cm column packed with Sepharose CL-2B as a carrier; Sepharose CL-2B has a dextran fractionation range of 100 to 20,000 kDa, and is available from, e.g., GE Healthcare; Sepharose CL-2B, CAS registry No. 65099-79-8, is a 2% crosslinked agarose with a particle size of 60 to 200 μm (measured by the laser diffraction scattering method))
Buffer: 0.1 M phosphate buffer (pH 7.1, containing 0.2 M NaCl)
Amount of applied sample: 4 mg (dissolved in 1 ml of buffer for use)
Flow rate: 0.15 mL/min
Amount of fraction: 1 mL/tube In addition, commercially available proteoglycan (hereinafter sometimes referred to as "PG-K") and commercially available glycosaminoglycan (chondroitin) (hereinafter sometimes referred to as "PG-M") were also subjected to gel filtration chromatography under the same conditions, and the amount of acidic saccharide contained in each eluted fraction was quantified. FIG. 3 shows the results.

As shown in FIG. 2, for an amount of eluate in the range of about 15 to 23 mL, a peak was observed for both saccharide and protein. Thus, it was found that this peak shows proteoglycan.

Next, each of the below-described various dextran molecular weight markers was also subjected to gel filtration chromatography under the same conditions as described above (except that the amount of sample was 1 mg), and the amount of saccharide (i.e., amount of dextran) contained in each eluted fraction was quantified by the phenol-sulfuric acid method. More specifically, the amount of saccharide was quantified as follows, according to the method described in Hodge, J. E. and Hofreiter, B. T., Methods in Carbohydrate Chemistry, 1, 338 (1962).

[1] 500 μl of a sample aqueous solution or a standard monosaccharide (mannose) aqueous solution was placed in a 105×15 mm test tube.
[2] 500 μl of a phenol reagent (5 v/v % aqueous phenol solution) was added thereto, and stirred.
[3] 2.5 ml of concentrated sulfuric acid was added thereto, and immediately stirred vigorously for 10 seconds.
[4] The mixture was left to stand for 20 minutes or more at room temperature.
[5] The absorption at 490 nm was measured with a spectrophotometer.

<Dextran Molecular Weight Markers>
Dextran from *Leuconostoc mesenteroides* (mol wt 5,000,000-40,000,000) (Sigma-Aldrich Co.) . . . for measuring void volume, 10000 kDa
Dextran Standard 1,400,000 (Sigma-Aldrich Co.) . . . 1400 kDa
Dextran Standard 670,000 (Sigma-Aldrich Co.) . . . 670 kDa
Dextran Standard 410,000 (Sigma-Aldrich Co.) . . . 410 kDa
Dextran Standard 270,000 (Sigma-Aldrich Co.) . . . 270 kDa The dextran marker from *Leuconostoc mesenteroides* was used for measuring the void volume of the Sepharose CL-2B packed column (upper limit of fractionation: 20,000 kDa). To more accurately measure the void volume, pretreatment was carried out to remove low-molecular weight dextran contained in the marker. The pretreatment was performed by eluting the dextran from *Leuconostoc mesenteroides* under the conditions described above in "Gel Filtration Chromatography Conditions," and collecting and freeze-drying fractions having a molecular weight of 20,000 kDa or more. More specifically, fractions consisting of the amount of eluate of from 15 to 19 mL, which corresponded to a first appeared peak, were collected and freeze-dried (it is believed that dextran having a molecular weight of 20,000 kDa or more was obtained by collecting and freeze-drying such fractions. Then, this freeze-dried product was applied to the column, and measured.

Figure 5:
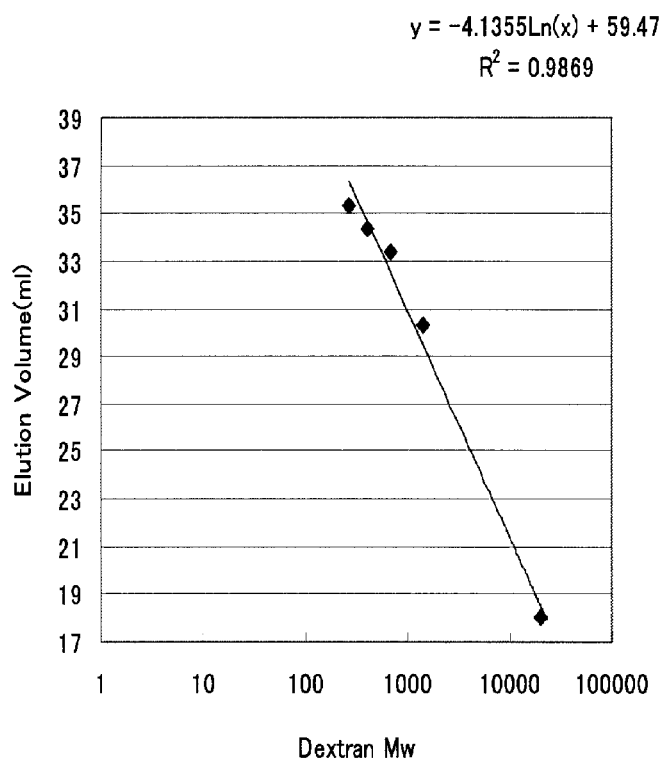

The resulting chromatograms are shown in FIGS. 4A to 4E. FIG. 4A shows measurement of the aforementioned pretreated freeze-dried product. Since the molecular weight of the pretreated product of dextran from *Leuconostoc mesenteroides* in FIG. 4A exceeds the fractionation range (100 kDa to 20000 kDa) of the Sepharose CL-2B packed column used, the amount of eluate corresponding to the peak top position was defined as the amount of eluate at which molecules of 20000 kDa, which is the exclusion limit of the column, are eluted. This amount of eluate is interpreted as indicating the void volume of the column. In each of FIGS. 4B to 4E, the amount of eluate corresponding to the position of the bisector of the peak area in the chromatogram designates the amount of eluate at which molecules of molecular weight of the marker are eluted. FIGS. 4B to 4E respectively show results of measurements for Dextran Standard 1,400,000, 670,000, 410,000, and 270,000. The relationship between these amounts of eluate and molecular weights were graphed, and a linear calibration curve was obtained (y=−4.1355 Ln(x)+59.47; $R^2$=0.9869) (FIG. 5). From this, it was confirmed that the molecular weights and the amounts of eluate obtained by the dextran molecular weight markers are highly correlated.

Furthermore, it was found from analysis results that there is a high possibility that an eluate before reaching the void volume contains proteoglycan (i.e., proteoglycan of greater than 20000 kDa, fractionation limit, exists). Since the fractionation range of the column used in the gel filtration chromatography was 100 kDa to 20000 kDa, it is highly possible that molecules of 20000 kDa or more were not accurately fractionated. Thus, as in the above, analysis by gel filtration chromatography under the following conditions was also performed using salmon nasal cartilage powder as a sample, and the amount of acidic saccharide in each fraction was quantified.

[Gel Filtration Chromatography Conditions]
Column: Sephacryl S-1000 SF packed column (φ1 cm×48 cm column packed with Sephacryl S-1000 SF as a carrier; Sephacryl S-1000 SF has a dextran fractionation range of $5\times10^5$ to $1\times10^8$ Da, and is available from, e.g., GE Healthcare)
Buffer: 0.1 M phosphate buffer (pH 7.1, containing 0.2 M NaCl)
Amount of applied sample: 4 mg
Flow rate: 0.3 mL/min
Amount of fraction: 1 mL/tube Furthermore, the below-described molecular weight markers were subjected to gel filtration chromatography under the same conditions. The amount of saccharide (i.e., amount of dextran) contained in each eluted fraction was quantified by the phenol-sulfuric acid method, and a calibration curve was prepared.

<Dextran Molecular Weight Markers>

Dextran from *Leuconostoc mesenteroides* (mol wt 5,000,000-40,000,000) (Sigma-Aldrich Co.) . . . 10000 kDa Dextran Standard 1,400,000 (Sigma-Aldrich Co.) . . . 1400 kDa Dextran Standard 670,000 (Sigma-Aldrich Co.) . . . 670 kDa The obtained calibration curve was as follows:

$y=-3.8743 \ln(x)+59.887$ ($R^2=0.9961$)

Figure 6:
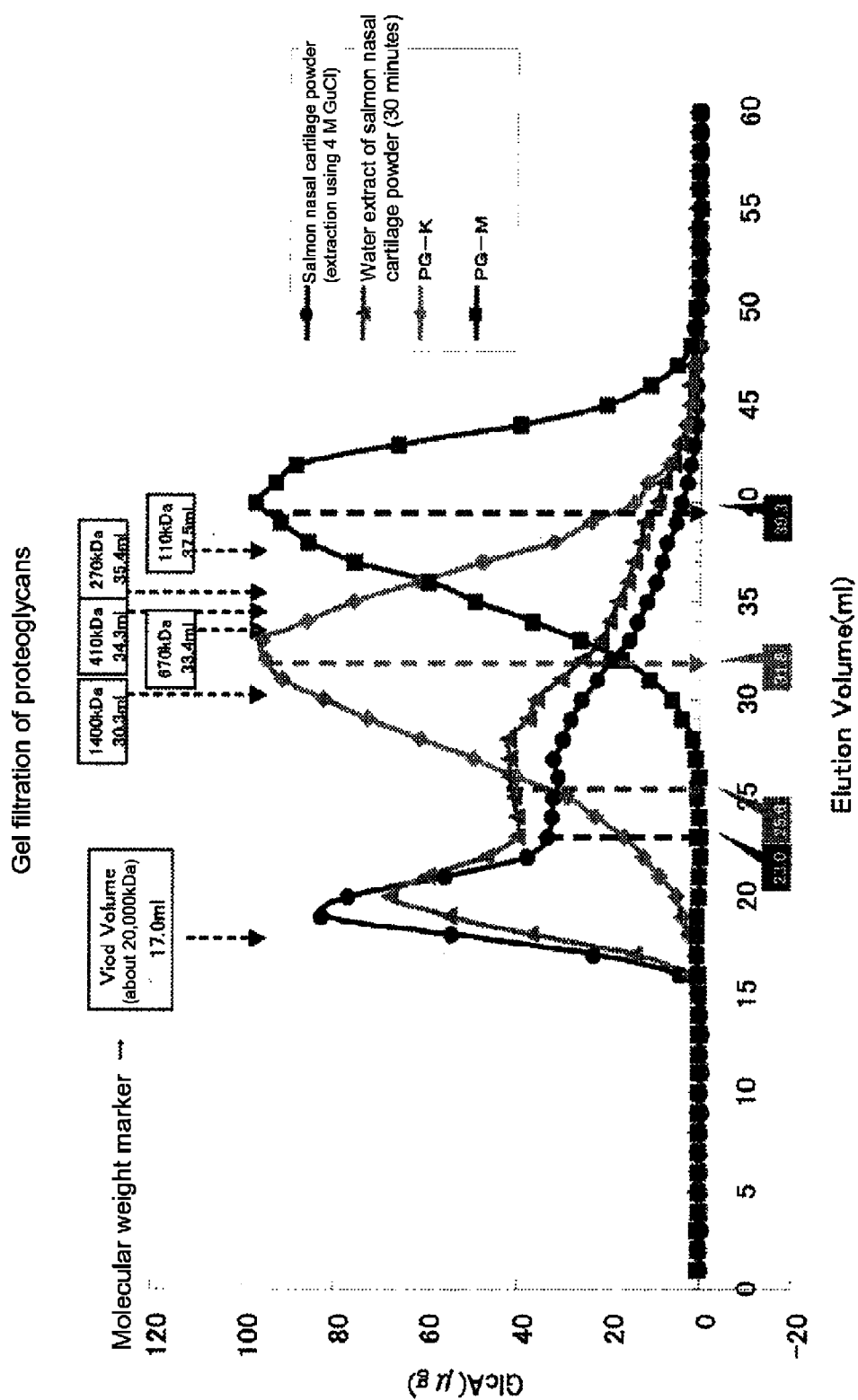

FIG. 6 is a graph that collectively shows the graphs of measurement results of acid saccharide amounts illustrated in FIGS. 2 and 3, and further shows the relationship between the molecular weights and the amounts of eluate obtained as described above. As mentioned above, regarding the salmon nasal cartilage powder and the water extract of salmon nasal cartilage powder, a peak appears in an amount of eluate in the range of about 15 to 23 mL in the gel filtration chromatography analysis. On the other hand, a peak appears in the range of about 28 to 49 mL for commercially available proteoglycan PG-M, and in the range of about 18 to 47 mL for commercially available PG-K. This shows that the salmon nasal cartilage powder and the water extract of salmon nasal cartilage powder (i.e., proteoglycan-containing materials of the present invention) contain very high molecular weight proteoglycan that is different from hitherto-known proteoglycan.

In addition, from the calibration curve shown in FIG. 5, it can be calculated that an amount of eluate of 23 mL corresponds to a molecular weight of about 6700 kDa. From this, the salmon nasal cartilage powder and the water extract of salmon nasal cartilage powder were found to contain proteoglycan of a molecular weight of about 6000 kDa or more.

Figure 7:
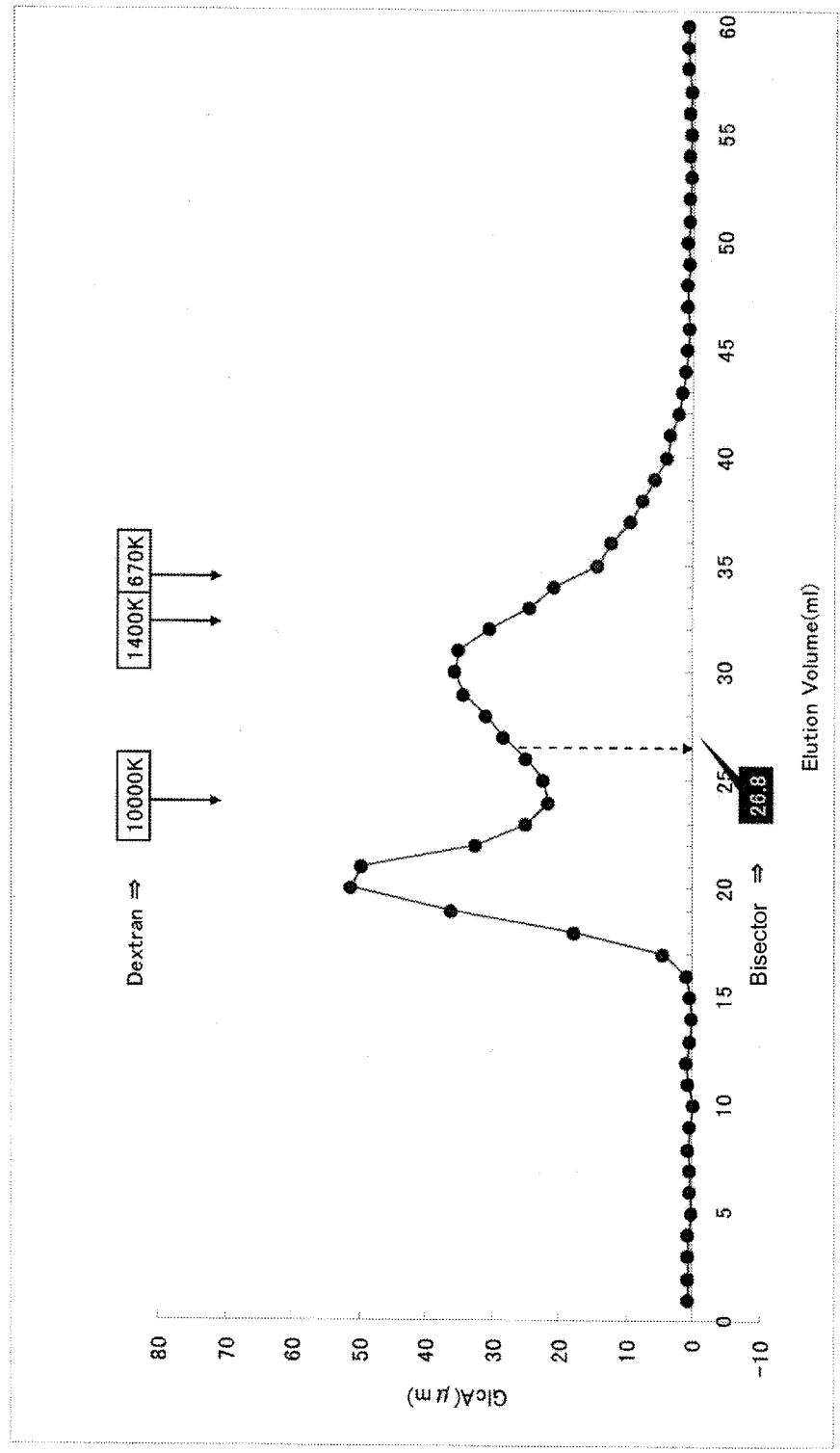

Furthermore, FIG. 7 shows the results of analysis of the salmon nasal cartilage powder using the Sephacryl S-1000 SF packed column. In FIG. 7, the rising of the proteoglycan peak from its first appearance in the chromatogram starts from an amount of eluate in the range of 15 to 16 mL. The molecular weight corresponding to this range of amount of eluate was calculated using the aforementioned calibration curve ($y=-3.8743 \ln(x)+59.887$), and determined to be about 90000 kDa. Thus, the salmon nasal cartilage powder was found to contain proteoglycan of about 90000 kDa.

From the above, it was confirmed that the salmon nasal cartilage powder contains proteoglycan of about 6000 to 90000 kDa.

Furthermore, using the calibration curve shown in FIG. 5, the mean molecular weight of proteoglycan in each sample was calculated from the amount of eluate at the peak position in each corresponding graph in FIG. 6. The mean molecular weight is commonly calculated from the amount of eluate at the position of the bisector of a peak area. However, since the proteoglycan peak in each chromatogram shown in FIG. 6 is nearly symmetrical in shape, the peak position was defined as a bisector position, and the mean molecular weight was calculated. More specifically, in consideration of experimental error and lot difference, values within ±1 mL of the amount of eluate at the peak position were regarded as y values of the calibration curve, and the range of the obtained x values was regarded as the mean molecular weight of proteoglycan in each sample. However, since the upper limit of fractionation range of the column used (Sepharose CL-2B packed column) was 20000 kDa, there is a possibility that the upper limit of the mean molecular weight of proteoglycan obtained from the analysis was not accurately calculated. Therefore, similarly, the mean molecular weight of proteoglycan was also determined from the results obtained when the Sephacryl S-1000 SF packed column was used. The results are shown in Table 1.

TABLE 1

| | Mean molecular weight of proteoglycan contained (Sepharose CL-2B packed column) | Mean molecular weight of proteoglycan contained (Sephacryl S-1000 SF packed column) |
|---|---|---|
| Salmon nasal cartilage powder | 12200 kDa to 19500 kDa | 22000 kDa to 38000 kDa |
| Water extract of salmon nasal cartilage powder | 9700 kDa to 15500 kDa | |
| PG-K | 480 kDa to 760 kDa | |
| PG-M | 90 kDa to 150 kDa (chondroitin) | |

It was found from the above results that the mean molecular weight of proteoglycan contained in the proteoglycan-containing materials of the present invention is about 9700 kDa to 38000 kDa.

Additionally, regarding the salmon nasal cartilage powder and the water extract of salmon nasal cartilage powder, the amount of eluate corresponding to the position where the area of the chromatogram obtained by the analysis with the Sepharose CL-2B packed column was bisected was determined (dotted arrows in FIG. 6), and the mean molecular weight was obtained from values within ±1 mL of the determined amount of eluate. As a result, the mean molecular weight of the mixture of acidic saccharide components in the salmon nasal cartilage powder was about 4800 kDa to 7700 kDa, and the mean molecular weight of the mixture of acidic saccharide components in the water extract of salmon nasal cartilage powder was about 1800 kDa to 4200 kDa.

Furthermore, regarding the salmon nasal cartilage powder, the amount of eluate corresponding to the position where the area of the chromatogram obtained by the analysis with the Sephacryl S-1000 SF packed column was bisected was determined (dotted arrow in FIG. 7), and the mean molecular weight was obtained from values within ±1 mL of the determined amount of eluate. As a result, the mean molecular weight of acidic saccharide components contained in the salmon nasal cartilage powder was about 3900 kDa to 6600 kDa.

Analysis of Skin Anti-Aging Effect of Proteoglycan-Containing Materials

Evaluation of Capability to Promote Cell Proliferation

Salmon nasal cartilage powder, a water extract of salmon nasal cartilage powder, and PG-K were used as samples, and their cell proliferation effects were analyzed. More specifically, the following experiment was carried out. In a culturing dish, human skin fibroblasts (HDF50: Cell Applications, Inc.) were seeded at $1.0 \times 10^4$ cells in minimum essential medium (MEM) containing 10% fetal bovine serum (FBS). Each sample was added individually to MEM to a concentration of 1 µg/mL or 10 µg/mL. Additionally, a medium to which nothing was added was used as a control. After the addition, the cells were cultured for five days. Following the culture, the MEM was removed, and the cells were detached and suspended with Trypsin-EDTA (Invitrogen). Afterward, Trypan blue stain (Sigma-Aldrich Co.) was added, and the number of cells was counted using a Burker-Turk counting chamber.

Figure 8:
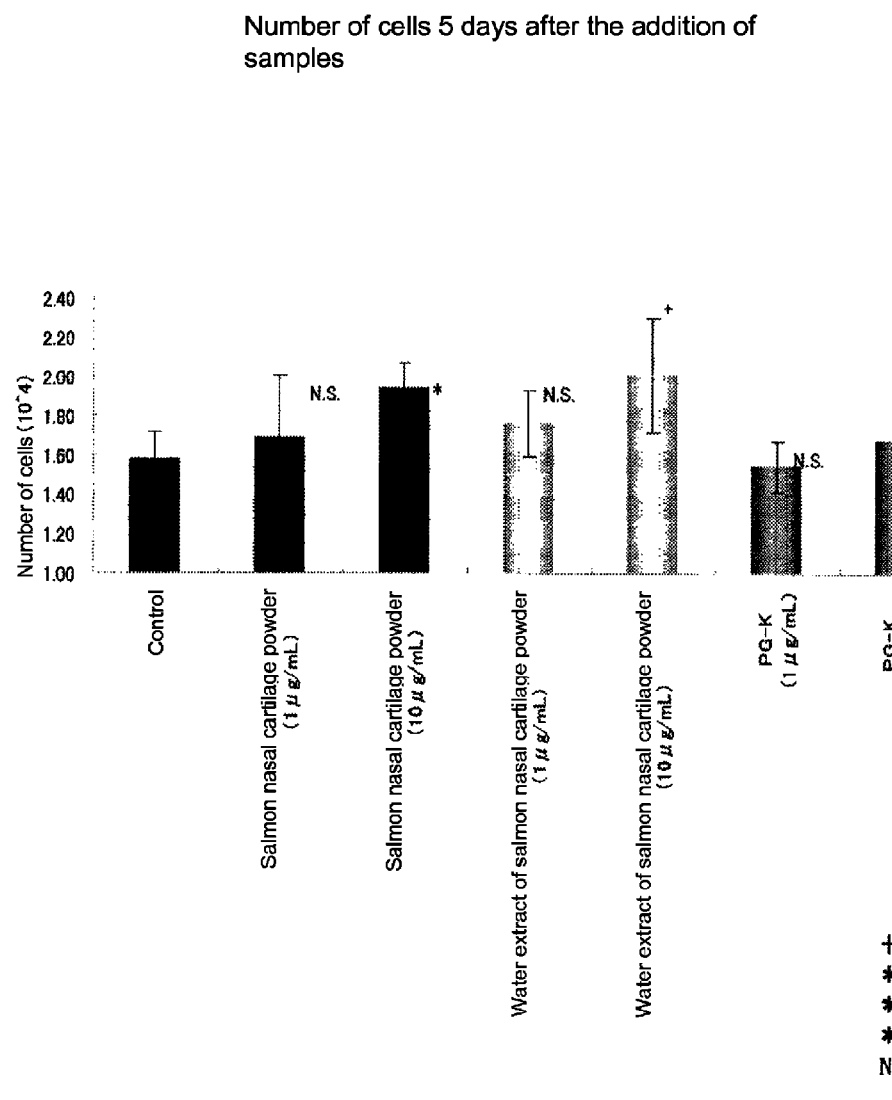

FIG. 8 shows the results. It was found from the results that the salmon nasal cartilage powder and the water extract of salmon nasal cartilage powder exhibit significant capability to proliferate human skin fibroblasts, while PG-K, a commercially available proteoglycan, does not exhibit the proliferation capability.

Moreover, as shown in FIG. 6, there is a great difference in the molecular weights of the contained components of PG-K, and the salmon nasal cartilage powder and the water extract of salmon nasal cartilage powder. In particular, in the chromatogram for PG-K, a peak for proteoglycan of large molecular weight, which exists in the chromatograms for the salmon nasal cartilage powder and the water extract of salmon nasal cartilage powder, is not seen. Thus, it seemed that the aforementioned capability to proliferate human skin fibroblasts is attributed to the proteoglycan of large molecular weight.

Evaluation of Moisturizing and Anti-Skin Aging-Capability through Ingestion
<Experimental Animal Used>

Hairless mice (Hr-/Kud ♂) (Kyudo Co., Ltd.) were used for an experiment. Male mice (four weeks old) that were free of the influence of fluctuations in estrogen on skin conditions were preliminarily fed, and then used for the experiment.
<Test Method>

The mice were placed in five feeding cages, as shown in Table 2 (six mice for one group). In addition, the subjects were marked on their tail portion to be individually identified. They continued to be preliminarily fed until they reached seven weeks of age.

TABLE 2

| Group | Abbreviation | Evaluation material | UVB irradiation |
|---|---|---|---|
| 1 | Co – UVB | Water (control) | Without |
| 2 | Co + UVB | Water (control) | With |
| 3 | HA + UVB | Hyaluronic acid | With |
| 4 | PG + UVB | Proteoglycan-containing material | With |
| 5 | PG/HA + UVB | Proteoglycan-containing material + hyaluronic acid | With |

<Preparation of Oral Administration Samples of Evaluation Materials>

A 2% dispersion of salmon nasal cartilage powder was prepared, and centrifugation was performed. The resulting supernatant was used as an administration sample of proteoglycan-containing material. This supernatant corresponds to a water extract of salmon nasal cartilage powder dissolved in water. The supernatant was evaporated to dryness to give solids. The supernatant contained about 0.7 mass % of water extract of salmon nasal cartilage powder. In addition, the amount of acidic saccharide components contained in the supernatant was quantified by the carbazole-sulfuric acid method. The amount of acidic saccharide components was about 0.17 mass % relative to the supernatant. Moreover, gel filtration chromatography analysis was conducted to determine the amount of proteoglycan contained in the supernatant from an area ratio of the obtained chromatogram. The amount of proteoglycan was about 0.07 mass % relative to the supernatant.

A 0.5 mass % aqueous solution of hyaluronic acid was prepared and used as an administration sample of hyaluronic acid. Additionally, a 1:1 liquid mixture (mass ratio) of the administration sample of proteoglycan-containing material and the administration sample of hyaluronic acid was used as an administration sample for coadministration of proteoglycan and hyaluronic acid. To the controls, distilled water was administered. Note that hyaluronic acid purchased from Nakahara, Co., Ltd. was used.
<Oral Administration Method>

When the hairless mice reached seven weeks of age, 0.5 mL of each administration sample was individually given once a day by forced oral administration using a sonde. This administration was continued at a frequency of five times per week (Monday to Friday) until the end of the experiment.

The amounts of the evaluation materials contained in each of the administration samples were as follows.

Hyaluronic acid: 2.5 mg/day

Proteoglycan-containing material: about 3.5 mg/day (acidic saccharide components: about 0.83 mg/day, proteoglycan: about 0.33 mg/day)

Proteoglycan-containing material+hyaluronic acid: about 1.75 mg/day of proteoglycan-containing material (acidic saccharide components: about 0.42 mg/day, proteoglycan: about 0.17 mg/day), and 1.25 mg/day of hyaluronic acid
<UVB Irradiation Method>

UVB irradiation started from four weeks after the start of the oral administration. The mice were placed in a cage for UVB irradiation. The cage was placed into an UVB irradiation device to carry out UVB irradiation five times per week (Monday to Friday), at an intensity of 1.0 mW/cm$^2$. The amount of irradiation was 60 mJ/cm$^2$ during only the first week after the start of the irradiation, and 120 mJ/cm$^2$ from the second week onward. The total amount of UVB irradiation during the 10-week period was 5.7 J/cm$^2$. Note that UVB was ultraviolet rays with wavelengths from 280 to 315 nm.
<Evaluation of Skin Barrier Functions>

Using a Tewameter, a multiprobe-type skin measuring instrument (MPA580: Courage-Khazaka), transepidermal water loss (TEWL) was measured at a frequency of once a week to evaluate skin barrier functions. Three areas on the back of each mouse were measured, and the average value was calculated. It is indicated that the larger the TEWL value, the lower the skin barrier functions (functions that prevent ingress of foreign matter from outside the skin into the body, and that prevent the escape of moisture inside the body to the outside).

Figure 9:
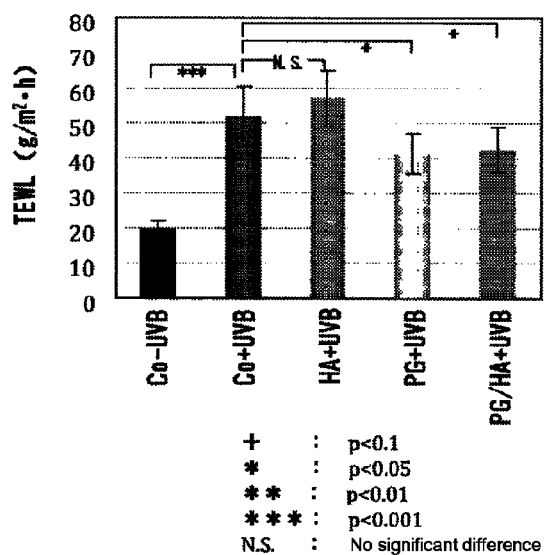

FIG. 9 shows the results of TEWL measurement eight weeks after the start of the UVB irradiation. In addition, Table 3 shows relative values of TEWL of mice Groups 3 to 5 four weeks, six weeks, and eight weeks after the start of the UVB irradiation, with respect to the TEWL value of an unirradiated control (Group 1: Co–UVB), which was assumed to be 100; and the TEWL value of an UVB-irradiated control (Group 2: Co+UVB), which was assumed to be 0. The relative values can be said to indicate a skin barrier improvement rate (%).

TABLE 3

| | <UVB Irradiation> | | |
|---|---|---|---|
| | 4 weeks | 6 weeks | 8 weeks |
| HA + UVB | −15 | −5 | −17 |
| PG + UVB | 5.2 | 3.7 | 34 |
| PG/HA + UVB | 36 | 35 | 30 |

It was found from these results that the proteoglycan-containing material from salmon nasal cartilage lowers the TEWL value, and improves skin barrier functions through oral administration (FIG. 9 and Table 3). Furthermore, it was found that ingestion of the proteoglycan-containing material from salmon nasal cartilage in combination with hyaluronic acid ensures the effect of improving skin barrier functions at an earlier stage (Table 3).

<Evaluation of Skin Elasticity>

Skin elasticity was measured with a Cutometer, a multi-probe-type skin-measuring instrument (MPA580: Courage-Khazaka). More specifically, four areas on the back of each mouse were measured, and elasticity (R2 value) was calculated by the following formula using the obtained Uf value and Ua value. Note that the Ua value represents return of the skin upon release from aspiration, and the Uf vale represents extensibility of the skin upon aspiration.

Elasticity (R2)=Ua/Uf

Figure 10:
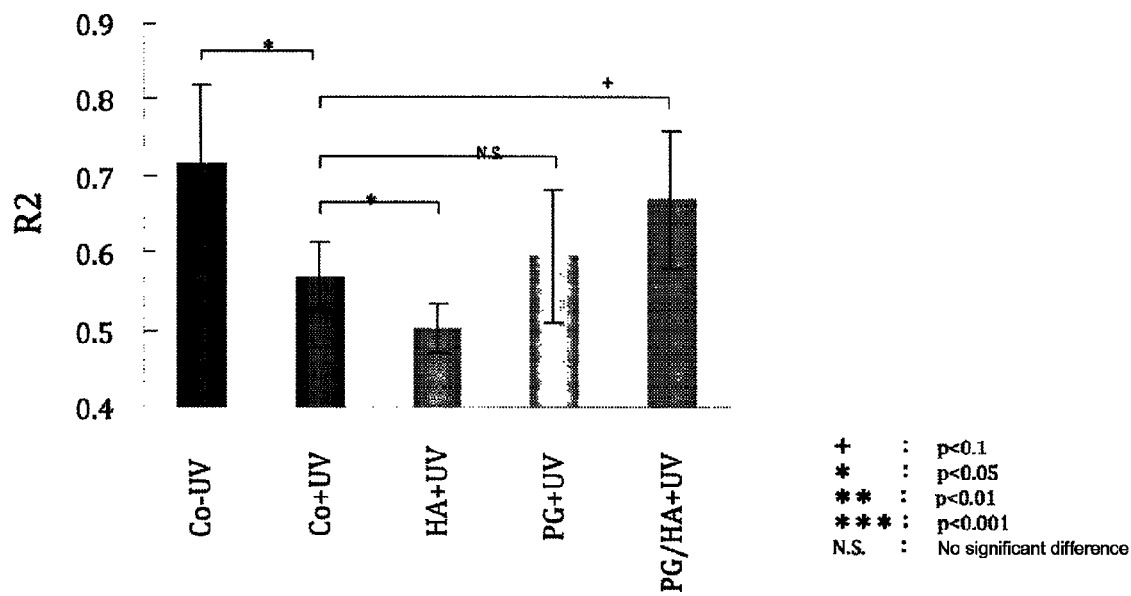

FIG. 10 shows the results of analysis conducted eight weeks after the start of the UVB irradiation (in FIG. 10, UVB is written as UV). It was suggested from the results that the proteoglycan-containing material from salmon nasal cartilage has an effect of improving skin elasticity through oral administration. Furthermore, it was shown that ingestion of the proteoglycan-containing material from salmon nasal cartilage in combination with hyaluronic acid significantly restores skin elasticity.

<Evaluation of Capability to Produce Collagen>

Ten weeks after the start of the UVB irradiation, skin tissue on the back of each mouse was collected. A portion of the back skin tissue was subjected to formalin fixation (for preparing skin tissue sections), and the rest was used for quantifying collagen.

The thus-obtained skin tissue (for quantifying collagen) was frozen and pulverized into powder with a cell grinder (auto mill, TK-AM5) (Tokken), and the powder was dried with a vacuum dryer. Protease inhibitor (P.I.) cocktail tablets (Complete Mini Easy Pack (Roche)) were dissolved in 0.5 M acetic acid. This acetic acid (containing P.I.) was added to the above skin tissue powder, and stirred at a low temperature. This was followed by centrifugation, and the supernatant portion (acid soluble collagen extract) was collected.

Then, the amount of collagen of the acid-soluble collagen extract was measured using a kit for quantifying acid-soluble collagen (Sircol Soluble Collagen Assay (Biocolor)) based on the manual.

Figure 11:
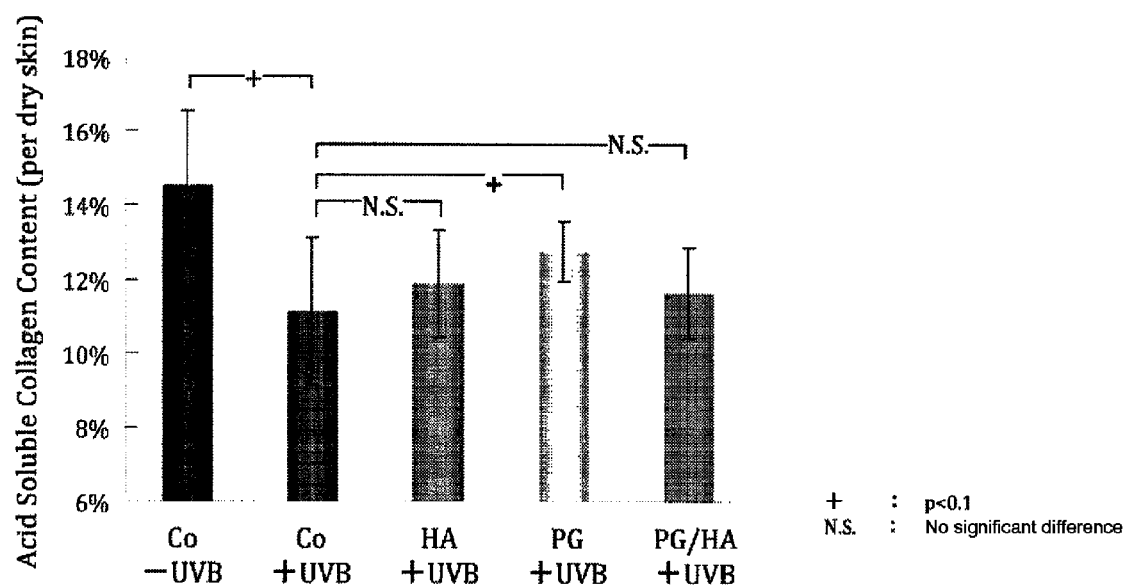

FIG. 11 shows the results. It was found from the results that the proteoglycan-containing material from salmon nasal cartilage significantly improves decrease in capability to produce collagen in the skin through oral administration.

<Analysis of Dermis-Thickening Inhibition Effect>

Using the aforementioned formalin-fixed tissue sections, paraffin-embedded blocks were prepared with an automatic paraffin fixation device (tissue processor (Tissue-Tek)). Sections were made with a microtome, stained with Hematoxylin-Eosin (HE), and used as samples.

Figure 12:
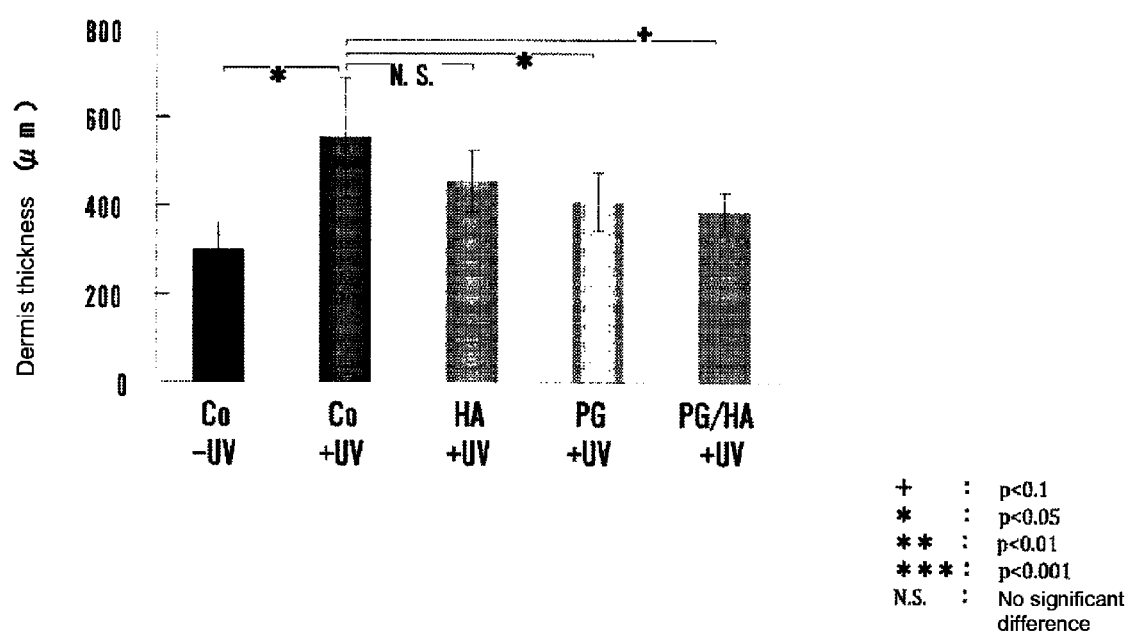

The samples were observed with an optical microscope, and images were saved on a digital camera. In each of the obtained images, the thickness of the dermal layer was measured at 10 locations. The average of the measurement values was calculated as the thickness of the dermal layer. FIG. 12 shows the results (in FIG. 12, UVB is written as UV). It was found from the results that the proteoglycan-containing material from salmon nasal cartilage significantly inhibits dermis-thickening through oral administration. Furthermore, it was shown that ingestion of the proteoglycan-containing material from salmon nasal cartilage in combination with hyaluronic acid enables dermis-thickening to be significantly inhibited, and that the inhibition capability is superior to that in cases where only the proteoglycan-containing material from salmon nasal cartilage was taken.

Evaluation of Moisturizing and Anti-Skin-Aging Capability by Applying to the Skin <Experimental Animal Used>

Hairless mice (Hr-/Kud ♂) (Kyudo Co., Ltd.) were used for an experiment. Male mice (four weeks old) that were free of the influence of fluctuations in estrogen on skin conditions were preliminarily fed, and then used for the experiment.

<Test Method>

The mice were placed in four feeding cages, as shown in Table 4 (five mice for one group). In addition, the subjects were marked on their tail portion to be individually identified. They continued to be preliminarily fed until they reached seven weeks of age.

TABLE 4

| Group | Abbreviation | Evaluation material (application sample) | UVB irradiation |
|---|---|---|---|
| 1 | Co − UVB | 0.5% xanthan gum aqueous solution (control) | Without |
| 2 | Co + UVB | 0.5% xanthan gum aqueous solution (control) | With |
| 3 | HA + UVB | 0.5% hyaluronic acid aqueous solution | With |
| 4 | PG + UVB | 0.5% salmon nasal cartilage powder aqueous solution | With |

<Evaluation of Skin Barrier Functions>

Figure 13:
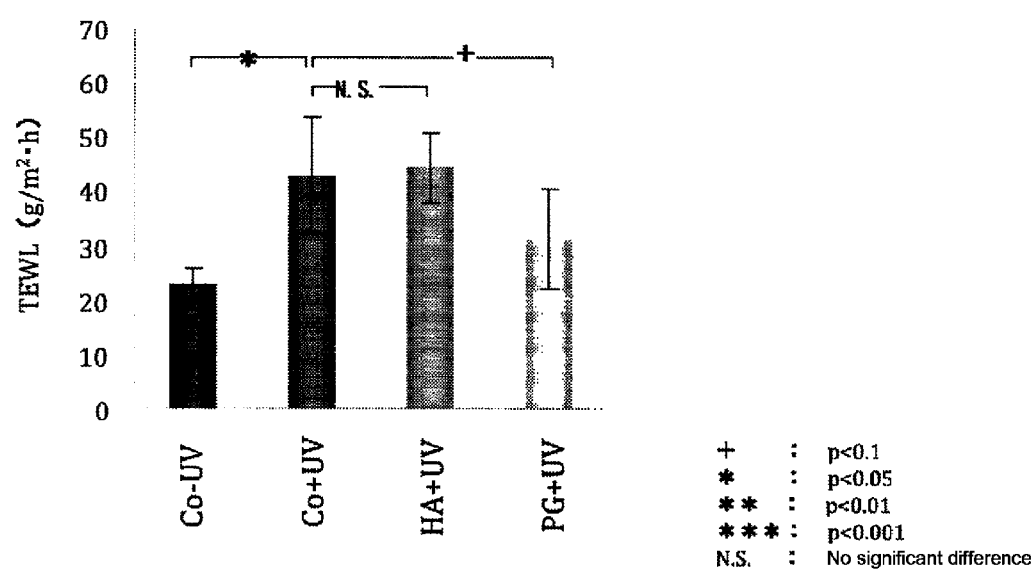

When the hairless mice reached seven weeks of age, 0.1 mL of one respective application sample was applied to the back of the mice once a day, and the hairless mice were subjected to UVB irradiation in the same manner as described in the section "Evaluation of Moisturizing and Anti-Skin Aging-Capability Through Ingestion" above. Five weeks after the start of the UVB irradiation, transepidermal water loss (TEWL) was measured in the same manner as described in the aforementioned section "Evaluation of Moisturizing and Anti-Skin Aging-Capability Through Ingestion." FIG. 13 shows the results (in FIG. 13, UVB is written as UV). It was found from the results that the proteoglycan-containing material from salmon nasal cartilage significantly lowers the TEWL value, and improves skin barrier functions by application to the skin.

As described above, it seemed that the capability to proliferate human skin fibroblasts is attributed to proteoglycan of large molecular weight, which is not contained in PG-K. In view of this, it appeared that various other effects are also attributed to the proteoglycan.

Figure 14:
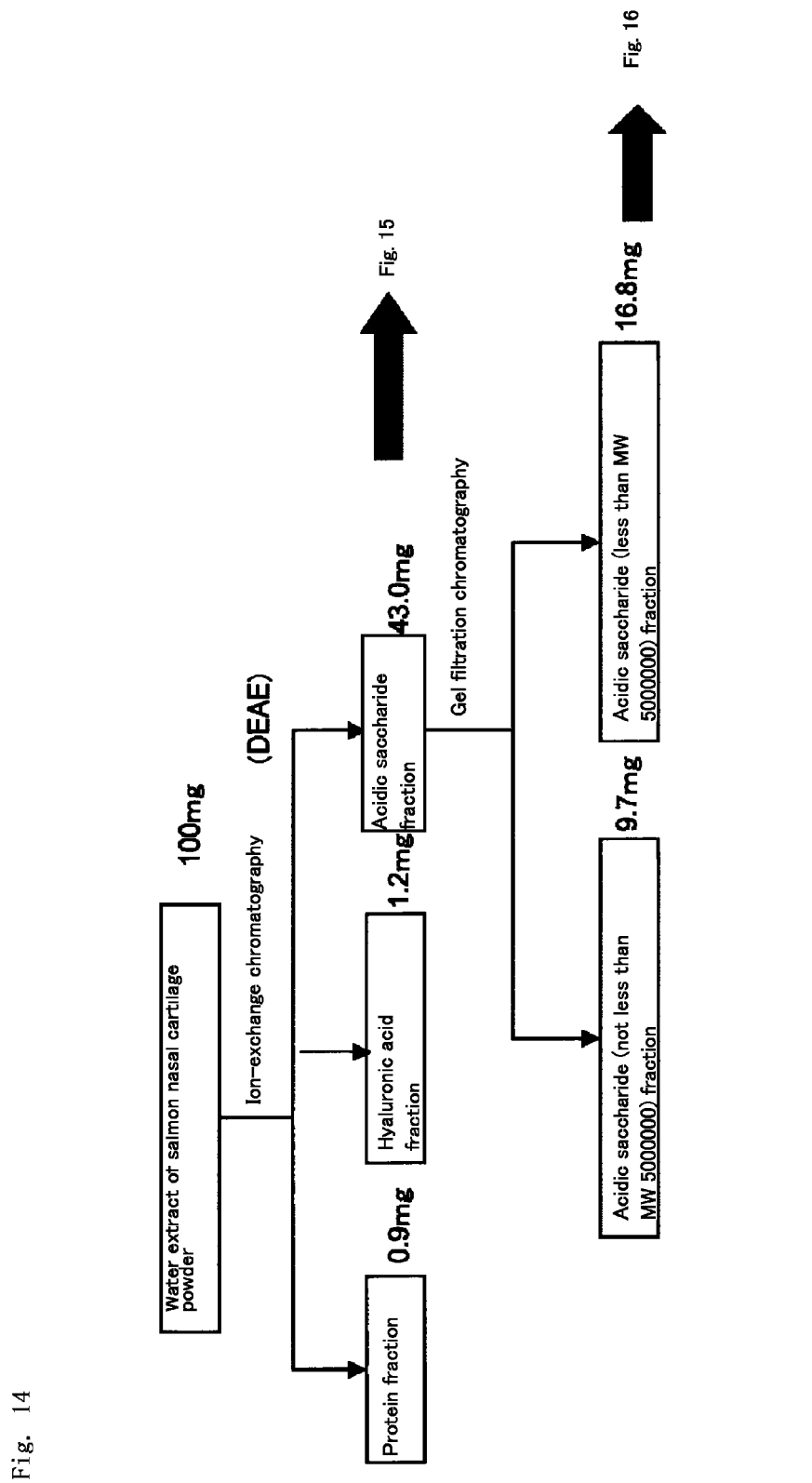

Fractionation of Water Extract of Salmon Nasal Cartilage Powder and Effect Verification A water extract of salmon nasal cartilage powder was fractionated using ion-exchange chromatography and gel filtration chromatography to analyze which fraction has a cell proliferation effect. FIG. 14 shows a procedure of the fractionation. The following are the fractionation conditions.

<Ion-Exchange Chromatography>

A φ5.0 cm×20 cm column was packed with a carrier (DEAE Sephacel (GE Healthcare)) to a height of 15 cm. Note that DEAE is an abbreviation of diethylaminoethyl.

As a solvent, 7 M urea-50 mM tris-hydrochloric acid buffer (pH 7.4) was used. Using a solvent in which 0 to 0.75 M sodium chloride was added to the above solvent, elution was performed by gradient-elution (linear gradient).

About 100 mg of a water extract of salmon nasal cartilage powder was dissolved in about 20 ml of the solvent. Afterward, an operation was carried out according to page 189 of Kiso Seikagaku Jikkenho (*Basic Biochemistry Experimental Method*), Vol. 5 (Shishitsu/Toshitsu/Fukugo Toshitsu (*Lipids/Carbohydrates/Complex Carbohydrates*)) edited by the Japanese Biochemical Society (Tokyo Kagaku Dojin); and the water extract of salmon nasal cartilage powder was fractionated into a protein fraction, a hyaluronic acid fraction, and a fraction of acidic saccharide with sulfate groups. Elution of the column was performed at a flow rate of 2.0 ml/min, and the volume of each of the individual fractions in the following combined fractions was 16 ml. In this case, the protein fraction was a combined fraction of Fraction Nos. 16 to 35; the hyaluronic acid fraction was a combined fraction of Fraction Nos. 37 to 42; and the fraction of acidic saccharide with sulfate groups was a combined fraction of Fraction Nos. 52 to 67. Although hyaluronic acid is also a kind of acidic saccharide, it does not have sulfate groups. Acidic saccharide (for example, chondroitin sulfate) contained in proteoglycan has sulfate groups. Additionally, since molecular polarity increases in the order of protein (in particular, collagen), hyaluronic acid, and acidic saccharide having sulfate groups, these three substances can be fractionated by ion exchange chromatography.

Protein was quantified by absorbance measurement at 280 nm. Hyaluronic acid was quantified using a Seikagaku Co. kit for quantifying hyaluronic acid. Acid saccharide having sulfate groups was quantified by the carbazole-sulfuric acid method.

The amounts of protein, hyaluronic acid, and acidic saccharide having sulfate groups that correspond to the case where 100 mg of the water extract of salmon nasal cartilage powder was isolated were 0.9 mg, 1.2 mg, and 43.0 mg, respectively.

Figure 15:
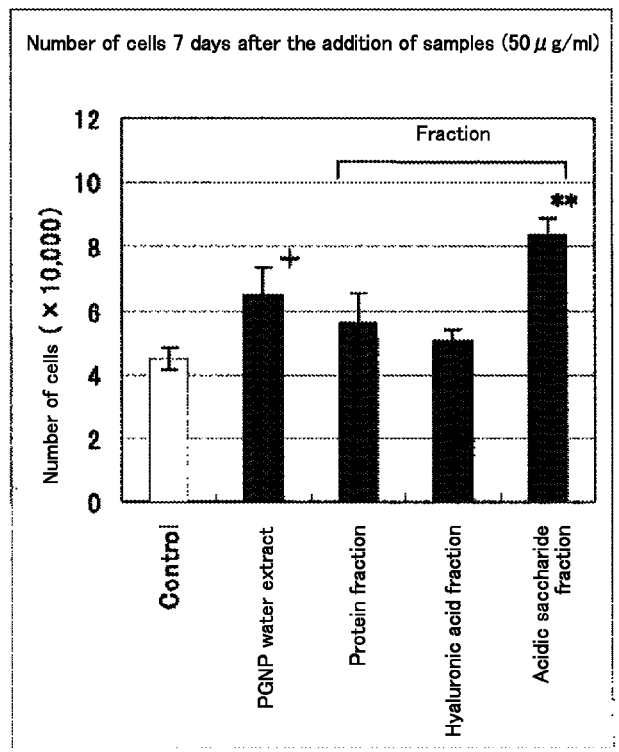

Four samples of the thus-obtained protein fraction, hyaluronic acid fraction, fraction of acidic saccharide with sulfate groups, and a water extract of salmon nasal cartilage powder were used, and the capability to proliferate human skin fibroblasts of each sample was analyzed in the same manner as in the section "Evaluation of Capability to Promote Cell Proliferation" above. FIG. 15 shows the results. Other than the water extract of salmon nasal cartilage powder, only the fraction of acidic saccharide with sulfate groups had significantly high capability to proliferate human skin fibroblasts with respect to the control. Moreover, the fraction of acidic saccharide with sulfate groups had high capability to proliferate human skin fibroblasts, even as compared with the water extract of salmon nasal cartilage powder. Hence, it seemed that the effect of proliferating human skin fibroblasts of the water extract of salmon nasal cartilage powder is attributed to acidic saccharide having sulfate groups. In addition, it appeared that this effect is attributable to proteoglycan, due to the fact that the fraction of acidic saccharide with sulfate groups is rich in proteoglycan.

Figure 16:
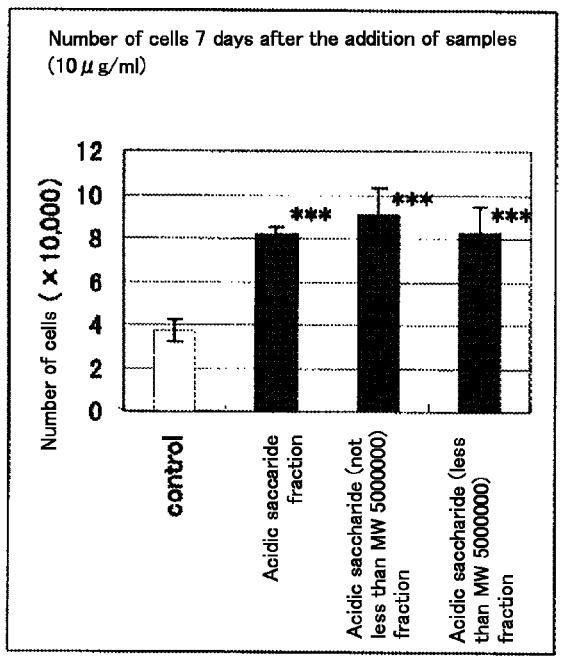

In FIGS. 14 to 16, the fraction of acidic saccharide with sulfate groups is simply written as "acidic saccharide fraction."

<Gel Filtration Chromatography>

43.0 mg of the fraction of acidic saccharide with sulfate groups obtained as described above was further fractionated by gel filtration chromatography. More specifically, under the gel filtration chromatography conditions using a Sepharose CL-2B packed column as described in the section "Analysis of Molecular Weight of Proteoglycan-Containing Materials" above, 1 ml of buffer was added per 5 mg of the fraction of acidic saccharide with sulfate groups, and dissolved to fractionate the fraction of acidic saccharide with sulfate groups into a fraction having a molecular weight of 5000 kDa or more, and a fraction having a molecular weight of less than 5000 kDa. The amount of acidic saccharide contained in each fraction was quantified by the carbazole-sulfuric acid method. The fraction having a molecular weight of 5000 kDa or more contained 9.7 mg of acidic saccharide, and the fraction having a molecular weight of less than 5000 kDa contained 16.8 mg of acidic saccharide.

FIG. 16 shows results in which the effect of proliferating human skin fibroblasts of these fractions was analyzed in the same manner as above. It was shown that the fraction having a molecular weight of 5000 kDa or more has a high effect of proliferating human skin fibroblasts, as compared to the fraction having a molecular weight of less than 5000 kDa. From the results, it appeared that the effect is largely attributable to proteoglycan. In particular, it seemed that proteoglycan of large molecular weight (molecular weight of 5000 kDa or more) contributes to the effect.

Note that the meanings of the marks "+," "," "*" in FIGS. 15 and 16 are the same as those in FIG. 8.

Formulation examples of oral compositions, cosmetic compositions, and food or beverage compositions according to the present invention are described below. Note that % indicates mass %. Formulation Examples 1 to 7 are for the cosmetic compositions; Formulation Examples 8 to 16 are for the food or beverage compositions; and Formulation Examples 17 to 22 are for the oral compositions.

Methods for producing proteoglycan-containing materials individually used in each of the following formulation examples are also described below.

<Proteoglycan-Containing Material A>

[1] Extraneous tissue such as skin or bone is removed from salmon nasal cartilage, and the resulting cartilage is crushed with a meat chopper.

[2] Tap water having a pH of 6.0 to 7.5 in an amount (volume) that is about double or triple the amount of the cartilage is added to the crushed salmon nasal cartilage, and sufficiently stirred at a temperature of 40° C. or below (room temperature).

[3] After the stirring, solids are separated and collected.

[4] Steps [2] and [3] are performed twice.

[5] The resulting solids are freeze-dried.

[6] The dried solids are finely pulverized with an atomizer mill.

[7] 95% ethanol in an amount (volume) that is about ten times the amount of the finely pulverized salmon nasal cartilage is added to the finely pulverized cartilage, and sufficiently stirred at a temperature of 40° C. or below.

[8] After the stirring, solids are separated and collected.

[9] Steps [7] and [8] are performed twice.

[10] The resulting solids are evaporated to dryness.

<Proteoglycan-Containing Material B>

[1] Purified water having a pH of 6.0 to 7.0 in an amount (volume) that is about ten times the amount of proteoglycan-containing material A is added to proteoglycan-containing material A, and sufficiently stirred at a temperature of 40° C. or below (room temperature) for about 30 minutes to 6 hours.

[2] After solids are separated and removed, the resulting solution is dried to obtain solids.

<Proteoglycan-Containing Material C>

[1] Purified water having a pH of 6.0 to 7.0 in an amount (volume) that is about ten times the amount of proteoglycan-containing material A is added to proteoglycan-containing material A, and sufficiently stirred at a temperature of 40° C.

or below (room temperature) for about 30 minutes to 6 hours. Then, solids are separated and removed, and an aqueous solution is obtained.

[2] Ethanol in an amount that is about five times the amount of the obtained aqueous solution is added to the aqueous solution, and sufficiently stirred at a temperature of 40° C. or below (room temperature).

[3] The resulting solids are collected and dried.

<Proteoglycan-Containing Material D>

[1] Extraneous tissue such as skin or bone is removed from salmon nasal cartilage, and the resulting cartilage is crushed with a meat chopper.

[2] Purified water having a pH of 6.5 to 7.5 in an amount (volume) that is about equal or double the amount of the cartilage is added to the crushed salmon nasal cartilage, and sufficiently stirred at a temperature of 40° C. or below (room temperature).

[3] After the stirring, solids are separated and collected.

[4] Steps [2] and [3] are performed three times.

[5] The resulting solids are finely pulverized with a wet grinder.

[6] 95% ethanol in an amount (volume) that is about ten times the amount of the finely pulverized salmon nasal cartilage is added to the finely pulverized cartilage, and sufficiently stirred at a temperature of 40° C. or below (room temperature).

[7] After the stirring, solids are separated and collected.

[8] Steps [6] and [7] are performed once.

[9] The resulting solids are evaporated to dryness.

[10] Purified water having a pH of 6.5 to 7.5 in an amount (volume) that is about ten times the amount of the dried product obtained in the above Step [9] is added to the dried product, and the dried product is immersed while stirring at a low temperature for about 12 to 48 hours.

[11] After the immersion, solids were separated and removed, and an aqueous solution is obtained.

[12] Ethyl alcohol in an amount that is about five times the amount of the aqueous solution was added to the aqueous solution, and sufficiently stirred at a temperature of 40° C. or below (room temperature).

[13] The resulting solids are collected and dried.

<Proteoglycan-Containing Material E>

[1] Extraneous tissue such as skin or bone is removed from salmon nasal cartilage, and the resulting cartilage is pulverized with a meat chopper.

[2] Tap water having a pH of 6.0 to 7.5 in an amount (volume) that is about five times the amount of the cartilage is added to the pulverized salmon nasal cartilage, and sufficiently stirred at a temperature of 40° C. or below (room temperature).

[3] After the stirring, solids are separated and collected.

[4] Steps [2] and [3] are performed twice.

[5] The resulting solids are finely pulverized with a wet grinder.

[6] 95% ethanol in an amount (volume) that is about five times the amount of the finely pulverized salmon nasal cartilage is added to the finely pulverized cartilage, and sufficiently stirred at a temperature of 40° C. or below (room temperature).

[7] After the stirring, solids are separated and collected.

[8] Steps [6] and [7] are performed twice.

[9] Purified water having a pH of 6.0 to 7.0 in an amount (volume) that is about equal or double the amount of the resulting solids is added to the solids, and sufficiently stirred at a temperature of 40° C. or below for about 30 minutes to 6 hours. Then, solids are separated and removed.

<Proteoglycan-Containing Material F>

[1] Extraneous tissue such as skin or bone is removed from salmon nasal cartilage, and the resulting cartilage is crushed with a wet grinder.

[2] Tap water having a pH of 6.0 to 7.5 in an amount (volume) that is about five times the amount of the cartilage is added to the crushed salmon nasal cartilage, and sufficiently stirred at a temperature of 40° C. or below (room temperature).

[3] After the stirring, solids are separated and collected.

[4] Steps [2] and [3] are performed twice.

[5] The resulting solids are finely pulverized with a wet grinder.

[6] Ethanol (product under standards of food additives) in an amount (volume) that is about five times the amount of the finely pulverized salmon nasal cartilage is added to the finely pulverized cartilage, and sufficiently stirred at a temperature of 40° C. or below (room temperature).

[7] After the stirring, solids are separated and collected.

[8] Steps [6] and [7] are performed twice.

[9] Purified water having a pH of 6.0 to 7.0 in an amount (volume) that is about five times the amount of the resulting solids was added to the solids, and sufficiently stirred at a temperature of 40° C. or below for about 30 minutes to 6 hours. Then, solids are separated and removed, and an aqueous solution is obtained.

[10] 95% ethanol in an amount that is about ten times the amount of the obtained aqueous solution is added to the aqueous solution, and sufficiently stirred at a temperature of 40° C. or below (room temperature). The resulting solids are collected and then evaporated to dryness.

<Proteoglycan-Containing Material G>

[1] Extraneous tissue such as skin or bone is removed from salmon nasal cartilage, and the resulting cartilage is crushed with a wet grinder.

[2] Tap water having a pH 6.0 to 7.5 in an amount (volume) that is about ten times the amount of the cartilage is added to the crushed salmon nasal cartilage, and sufficiently stirred at a temperature of 40° C. or below (room temperature).

[3] After the stirring, solids are separated and collected.

[4] Steps [2] and [3] are performed twice.

[5] The resulting solids are finely pulverized with a wet grinder.

[6] 95% ethanol in an amount (volume) that is about three times the amount of the finely pulverized salmon nasal cartilage was added to the finely pulverized cartilage, and sufficiently stirred at a temperature of 40° C. or below (room temperature).

[7] After the stirring, solids are separated and collected.

[8] Steps [6] and [7] are performed three times.

[9] Purified water having a pH of 6.0 to 7.0 in an amount (volume) that is about double or triple the amount of the resulting solids is added to the solids, and sufficiently stirred at a temperature of 40° C. or below for about 30 minutes to 6 hours. Then, solids are separated and removed, and an aqueous solution is obtained.

[10] Sodium chloride is added to the aqueous solution after the separation, and the solution is saturated with sodium chloride.

[11] 95% ethanol in an amount that is about five times the amount of the aqueous solution is added to the aqueous solution, and sufficiently stirred at a temperature of 40° C. or below (room temperature). The resulting solids are collected and then evaporated to dryness.

Regarding proteoglycan-containing materials A to D, the amount of acidic saccharide in each material was determined by the carbazole-sulfuric acid method, and the amount of proteoglycan in each material was determined from the area ratio of each corresponding chromatogram. The mass ratio of acidic saccharide and proteoglycan to each material on a dry mass basis is as follows.

A: Acidic saccharide: about 35% Proteoglycan: about 15%
B: Acidic saccharide: about 45% Proteoglycan: about 18%
C: Acidic saccharide: about 55% Proteoglycan: about 23%
D: Acidic saccharide: about 60% Proteoglycan: about 24%

Formulation Examples

Formulation Example 1

Lotion

| Components | Amount % |
|---|---|
| Proteoglycan-containing material E | 5.0 |
| Ethyl alcohol | 20.0 |
| 1,3-butylene glycol | 5.0 |
| Phenoxyethanol | 0.7 |
| Oxyethylene hydrogenated castor oil (60 E.O.) | 0.3 |
| Oxyethylene hydrogenated castor oil (40 E.O.) | 0.05 |
| Citric acid | 0.08 |
| Sodium citrate | 0.08 |
| Polyethylene glycol (mean molecular weight: one million) | 0.03 |
| Perfume | 0.03 |
| Purified water | Balance |
| Total | 100.0 |

Formulation Example 2

Serum

| Components | Amount % |
|---|---|
| Proteoglycan-containing material G | 2.0 |
| Ethyl alcohol | 10.0 |
| Concentrated glycerin | 10.0 |
| 1,3-butylene glycol | 6.0 |
| Phenoxyethanol | 0.7 |
| Oxyethylene hydrogenated castor oil (60 E.O.) | 0.5 |
| Hydrogenated soybean phospholipid | 0.5 |
| Xanthan gum | 0.4 |
| Citric acid | 0.08 |
| Sodium citrate | 0.08 |
| Perfume | 0.1 |
| Purified water | Balance |
| Total | 100.0 |

Formulation Example 3

Emulsion

| Components | Amount % |
|---|---|
| Proteoglycan-containing material D | 0.2 |
| Ethyl alcohol | 10.0 |
| 1,3-butylene glycol | 5.0 |
| Concentrated glycerin | 5.0 |
| Carboxyvinyl polymer | 0.5 |
| Phenoxyethanol | 0.5 |
| Oxyethylene hydrogenated castor oil (60 E.O.) | 0.3 |
| Potassium hydroxide | 0.3 |
| Polyoxyethylene hydrogenated castor oil (40 E.O.) | 0.1 |
| Citric acid | 0.05 |
| Sodium citrate | 0.05 |
| Disodium edetate | 0.05 |
| Perfume | 0.1 |
| Purified water | Balance |
| Total | 100.0 |

Formulation Example 4

Cream

| Components | Amount % |
|---|---|
| Proteoglycan-containing material A | 5.5 |
| Concentrated glycerin | 10.0 |
| Olive oil | 8.0 |
| Squalane | 6.0 |
| Polyglyceryl monostearate | 4.0 |
| Lipophilic glyceryl monostearate | 4.0 |
| Stearic acid | 4.0 |
| Ethyl alcohol | 3.0 |
| Cetanol | 3.0 |
| Carboxyvinyl polymer | 0.2 |
| Potassium hydroxide | 0.6 |
| Perfume | 0.1 |
| Purified water | Balance |
| Total | 100.0 |

Formulation Example 5

Hair Restorer

| Components | Amount % |
|---|---|
| Proteoglycan-containing material C | 0.05 |
| Polyoxyethylene hydrogenated castor oil (60 E.O.) | 0.5 |
| Xanthan gum | 0.3 |
| Pyridoxine hydrochloride | 0.2 |
| Benzyl nicotinate | 0.02 |
| 1-menthol | 0.1 |
| Perfume | 0.03 |
| Purified water | Balance |
| Total | 100.0 |

Formulation Example 6

Hair Tonic

| Components | Amount % |
|---|---|
| Proteoglycan-containing material F | 0.005 |
| Ethyl alcohol | 50.0 |
| Xanthan gum | 0.3 |
| Acrylic resin alkanolamine liquid | 0.1 |

Formulation Example 7

Lotion for Decreasing the Sizes of Pores of the Skin

| Components | Amount % |
| --- | --- |
| Proteoglycan-containing material B | 0.1 |
| Ethyl alcohol | 15.0 |
| Xanthan gum | 0.15 |
| 1,3-butylene glycol | 5.0 |
| Purified water | Balance |
| Total | 100.0 |

Formulation Example 8

Powdered Brown Rice Beverage

| Components | Amount % |
| --- | --- |
| Proteoglycan-containing material C | 23.0 |
| Black sesame paste | 15.0 |
| Powdered brown sugar | 8.0 |
| Soybean powder | Balance |
| Total | 100.0 |

Formulation Example 9

Tablet

| Components | Amount % |
| --- | --- |
| Proteoglycan-containing material D | 40.0 |
| Maltitol | 10.0 |
| Lactose | 36.0 |
| Sucrose fatty acid ester | 5.0 |
| Calcium stearate | 4.0 |
| Silicon dioxide | 4.0 |
| Powder flavor | 1.0 |
| Total | 100.0 |

Formulation Example 10

Powdered Food

| Components | Amount % |
| --- | --- |
| Proteoglycan-containing material B | 5.5 |
| Fructose | 30.0 |
| Dextrin | 52.4 |

-continued

| Components | Amount % |
| --- | --- |
| 1-menthol | 0.2 |
| Perfume | 0.01 |
| Purified water | Balance |
| Total | 100.0 |

-continued

| Components | Amount % |
| --- | --- |
| Peppermint flavor | 3.0 |
| Ascorbic acid | 2.5 |
| Sucralose | 0.1 |
| Lemon flavor | 2.0 |
| Total | 100.0 |

Formulation Example 11

Pill

| Components | Amount % |
| --- | --- |
| Proteoglycan-containing material A | 23.0 |
| Galactose | 30.0 |
| Erythritol | 10.0 |
| Sucralose | 0.06 |
| Citric acid | 5.0 |
| 1-menthol | 1.0 |
| Sucrose fatty acid ester | 5.0 |
| Crystalline cellulose | Balance |
| Total | 100.0 |

Formulation Example 12

Candy

| Components | Amount % |
| --- | --- |
| Proteoglycan-containing material E | 0.5 |
| Reducing maltose starch syrup | 52.0 |
| Lactose | 10.0 |
| Citric acid | 7.0 |
| Peppermint flavor | 1.5 |
| Spearmint flavor | 1.0 |
| Peach flavor | 2.5 |
| Purified water | Balance |
| Total | 100.0 |

Formulation Example 13

Chewable Tablet

| Components | Amount % |
| --- | --- |
| Proteoglycan-containing material G | 1.0 |
| Glucose | 30.0 |
| Erythritol | 20.0 |
| Sucrose fatty acid ester | 4.0 |
| Aspartame | 0.15 |
| Spearmint flavor | 3.0 |
| Crystalline cellulose | Balance |
| Total | 100.0 |

Formulation Example 14

Powdered Tea

| Components | Amount % |
| --- | --- |
| Proteoglycan-containing material F | 0.01 |
| Oolong tea water extract powder | 10.0 |
| *Coix lacryma-jobi* var. *ma-yuen* water extract powder | 5.0 |
| Green tea water extract powder | 5.0 |
| Glucose | 10.0 |
| Sucralose | 0.1 |
| Dextrin | Balance |
| Total | 100.0 |

Formulation Example 15

Capsule

| Components | Amount % |
| --- | --- |
| Proteoglycan-containing material D | 80.0 |
| Crystalline cellulose | 20.0 |
| Total | 100.0 |

Formulation Example 16

Chewing Gum

| Components | Amount % |
| --- | --- |
| Proteoglycan-containing material B | 0.05 |
| Gum base | 20.0 |
| Reducing starch syrup | 18.0 |
| Flavor | 1.0 |
| Powdered sugar | Balance |
| Total | 100.0 |

Formulation Example 17

Oral Gel

| Components | Amount % |
| --- | --- |
| Proteoglycan-containing material B | 0.05 |
| Glycerin | 10.0 |
| Propylene glycol | 5.0 |
| Hydroxyethyl cellulose | 1.0 |
| Polyoxyethylene (60) hydrogenated castor oil | 0.2 |
| Xanthan gum | 0.2 |
| Flavor | 0.1 |
| Ethyl p-hydroxybenzoate | 0.1 |
| Saccharin sodium | 0.01 |
| Purified water | Balance |
| Total | 100.0 |

Formulation Example 18

Oral Embrocation

| Components | Amount % |
| --- | --- |
| Proteoglycan-containing material D | 5.0 |
| Shellac | 10.0 |
| Ethyl alcohol | 40.0 |
| Hydroxyethyl cellulose | 0.3 |
| Flavor | 2.0 |
| Purified water | Balance |
| Total | 100.0 |

Formulation Example 19

Mouthwash

| Components | Amount % |
| --- | --- |
| Proteoglycan-containing material F | 0.01 |
| Glycerin | 10.0 |
| Propylene glycol | 3.0 |
| Polyoxyethylene (40) hydrogenated castor oil | 0.4 |
| Flavor | 0.1 |
| pH regulator | Suitable amount |
| Purified water | Balance |
| Total | 100.0 |

Formulation Example 20

Liquid Dentifrice

| Components | Amount % |
| --- | --- |
| Proteoglycan-containing material C | 0.02 |
| Glycerin | 11.0 |
| Propylene glycol | 3.0 |
| Polyoxyethylene (60) hydrogenated castor oil | 0.4 |
| Flavor | 0.1 |
| Saccharin sodium | 0.01 |
| pH regulator | Suitable amount |
| Purified water | Balance |
| Total | 100.0 |

Formulation Example 21

Dentifrice

| Components | Amount % |
| --- | --- |
| Proteoglycan-containing material A | 14.5 |
| Sorbitol | 45.0 |
| Abrasive silica | 18.0 |
| Thickening silica | 3.0 |
| Polyethylene glycol 400 | 3.0 |

-continued

| Components | Amount % |
|---|---|
| Flavor | 1.0 |
| Polyoxyethylene (40) hydrogenated castor oil | 0.5 |
| Sodium carboxymethylcellulose | 0.4 |
| Saccharin sodium | 0.2 |
| pH regulator | Suitable amount |
| Purified water | Balance |
| Total | 100.0 |

Formulation Example 22

Mouth Spray

| Components | Amount % |
|---|---|
| Proteoglycan-containing material G | 0.01 |
| Ethanol | 30.0 |
| Glycerin | 10.0 |
| Polyoxyethylene (60) hydrogenated castor oil | 1.0 |
| Flavor | 1.0 |
| l-menthol | 0.5 |
| Saccharin sodium | 0.1 |
| pH regulator | Suitable amount |
| Purified water | Balance |
| Total | 100.0 |

The invention claimed is:

1. A method for improving skin elasticity, comprising orally administering a composition comprising a proteoglycan-containing material obtained from salmon cartilage by water extraction, wherein the proteoglycan-containing materials comprises acidic saccharide components, and the acidic saccharide components comprise proteoglycan and acidic saccharide,
   the proteoglycan-containing material comprising, on a dry mass basis, 15 to 70 mass % of acidic saccharide components, 55 mass % or more of the acidic saccharide components having a molecular weight of not less than 2000 kDa, and
   the proteoglycan-containing material further comprising proteoglycan having a molecular weight of not less than 5000 kDa.

2. The method according to claim 1, comprising orally administering the composition and hyaluronic acid.

3. The method according to claim 1, wherein the proteoglycan-containing material comprises an acidic saccharide component having a molecular weight of not less than 5000 kDa.

4. The method according to claim 1, wherein 20 mass % or more of the acidic saccharide components have a molecular weight of not less than 10000 kDa.

5. The method according to claim 1, wherein the proteoglycan-containing material comprises 60 mass % or more of acidic saccharide components having a molecular weight of not less than 2000 kDa.

6. The method according to claim 1, wherein the salmon cartilage is a salmon nasal cartilage.

* * * * *